United States Patent [19]
Yoon

[11] Patent Number: 5,842,971
[45] Date of Patent: Dec. 1, 1998

[54] OPTICAL ENDOSCOPIC PORTALS AND METHODS OF USING THE SAME TO ESTABLISH PASSAGES THROUGH CAVITY WALLS

[76] Inventor: InBae Yoon, 2101 Highland Ridge Dr., Phoenix, Md. 21131

[21] Appl. No.: 936,205

[22] Filed: Sep. 22, 1997

Related U.S. Application Data

[63] Continuation-in-part of Ser. No. 651,284, May 22, 1996.

[51] Int. Cl.[6] .................................................... A61B 1/012
[52] U.S. Cl. .......................... 600/101; 600/140; 600/144
[58] Field of Search .................................... 600/139, 140, 600/143, 121, 144, 101

[56] References Cited

U.S. PATENT DOCUMENTS

| | | |
|---|---|---|
| 4,236,509 | 12/1980 | Takahashi et al. ...................... 600/139 |
| 4,254,762 | 3/1981 | Yoon . |
| 4,392,485 | 7/1983 | Hiltebrandt . |
| 4,535,773 | 8/1985 | Yoon . |
| 4,607,622 | 8/1986 | Fritch et al. . |
| 4,714,075 | 12/1987 | Kravter et al. .......................... 600/140 |
| 4,788,967 | 12/1988 | Ueda . |
| 4,807,598 | 2/1989 | Hasegawa . |
| 4,944,287 | 7/1990 | Takahashi et al. ...................... 600/146 |
| 5,179,934 | 1/1993 | Nagayoshi et al. . |
| 5,197,457 | 3/1993 | Adair ..................................... 600/143 |
| 5,307,803 | 5/1994 | Matsuura et al. ........................ 600/140 |
| 5,334,150 | 8/1994 | Kaali . |
| 5,376,076 | 12/1994 | Kaali . |
| 5,380,291 | 1/1995 | Kaali . |
| 5,385,572 | 1/1995 | Nobles et al. . |
| 5,407,423 | 4/1995 | Yoon ....................................... 604/286 |
| 5,419,312 | 5/1995 | Arenberg et al. . |
| 5,429,609 | 7/1995 | Yoon ....................................... 604/167 |
| 5,467,762 | 11/1995 | Sauer et al. . |
| 5,554,098 | 9/1996 | Yabe et al. . |
| 5,562,696 | 10/1996 | Nobles et al. . |
| 5,569,160 | 10/1996 | Sauer et al. . |
| 5,569,291 | 10/1996 | Privitera et al. . |
| 5,569,292 | 10/1996 | Scwemberger et al. . |
| 5,591,120 | 1/1997 | Machida et al. ......................... 600/139 |
| 5,591,192 | 1/1997 | Privitera et al. . |
| 5,609,562 | 3/1997 | Kaali . |
| 5,628,794 | 5/1997 | Lindstrom . |
| 5,629,360 | 5/1997 | Askari et al. . |
| 5,635,482 | 6/1997 | Bhatnagar . |
| 5,637,165 | 6/1997 | Chen . |
| 5,639,908 | 6/1997 | Lai . |
| 5,683,348 | 11/1997 | Diener ..................................... 600/139 |

*Primary Examiner*—Paul J. Hirsch

[57] ABSTRACT

An optical endoscopic portal for providing a passage through a body cavity wall includes a cannula comprising an absorbent member having a distal end for positioning in a body cavity, a proximal end for positioning external of the body cavity and a passage between the distal and proximal ends for receiving instruments. The absorbent member has a rigid dry state prior to introduction through the cavity wall and a soft wet state after absorbing fluid upon introduction of the distal end in the body cavity. An optical element is disposed in the absorbent material and optically couples the distal end with the proximal end. The optical element includes a light transmitting optical element for illuminating the body cavity and/or an image transmitting optical element for transmitting an image of the body cavity for viewing externally thereof. A method of establishing a passage through a cavity wall includes the steps of introducing an elongate member of absorbent material in a small size opening in a cavity wall with the elongate member in a rigid dry state such that the elongate member extends longitudinally through the cavity wall, absorbing fluid with the absorbent material to place the elongate member in a soft wet state, illuminating the body cavity with light and/or transmitting an image of the body cavity for external viewing with an optical element disposed in the absorbent material and introducing an instrument through a passage of the elongate member to position a distal end of the instrument in the body cavity.

63 Claims, 21 Drawing Sheets

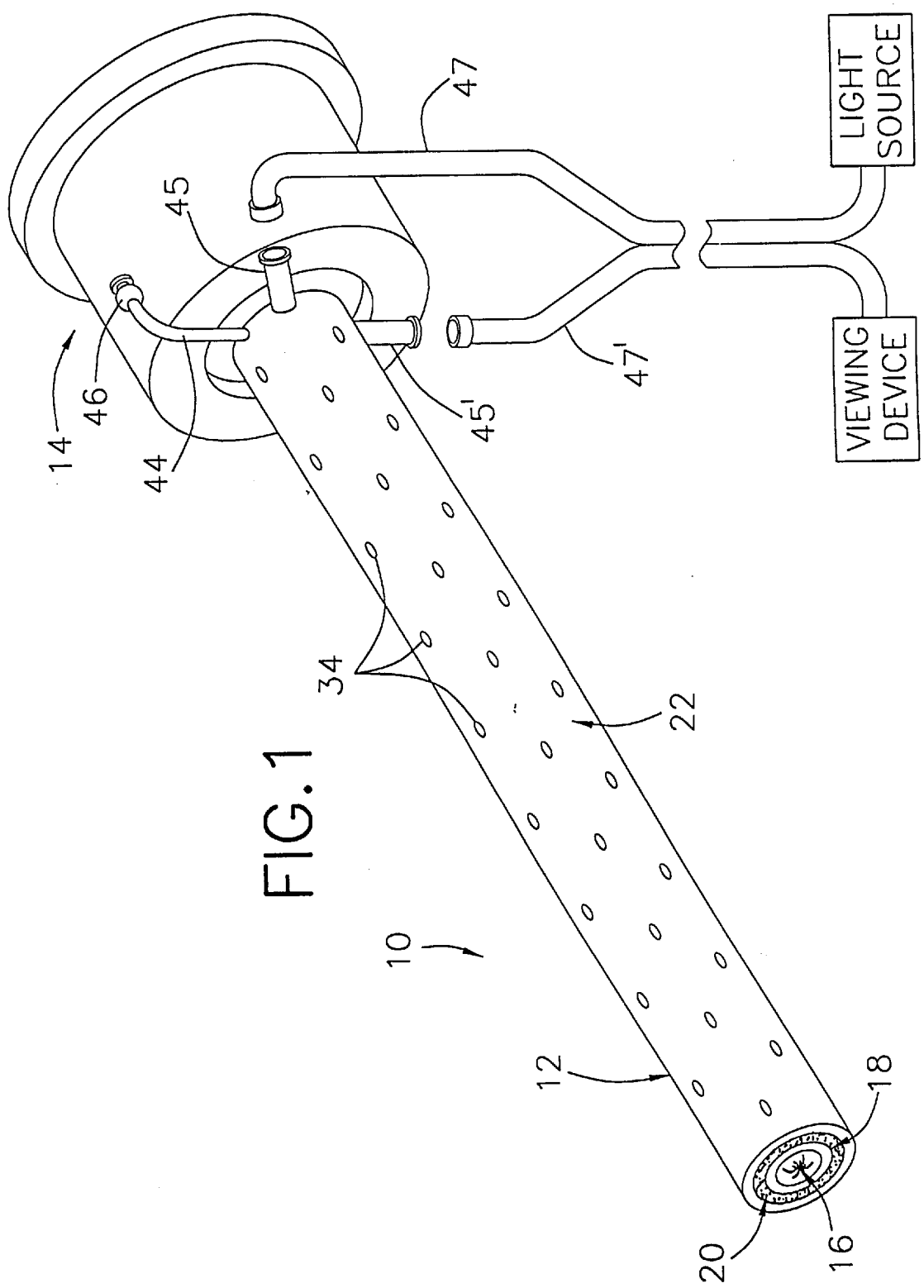

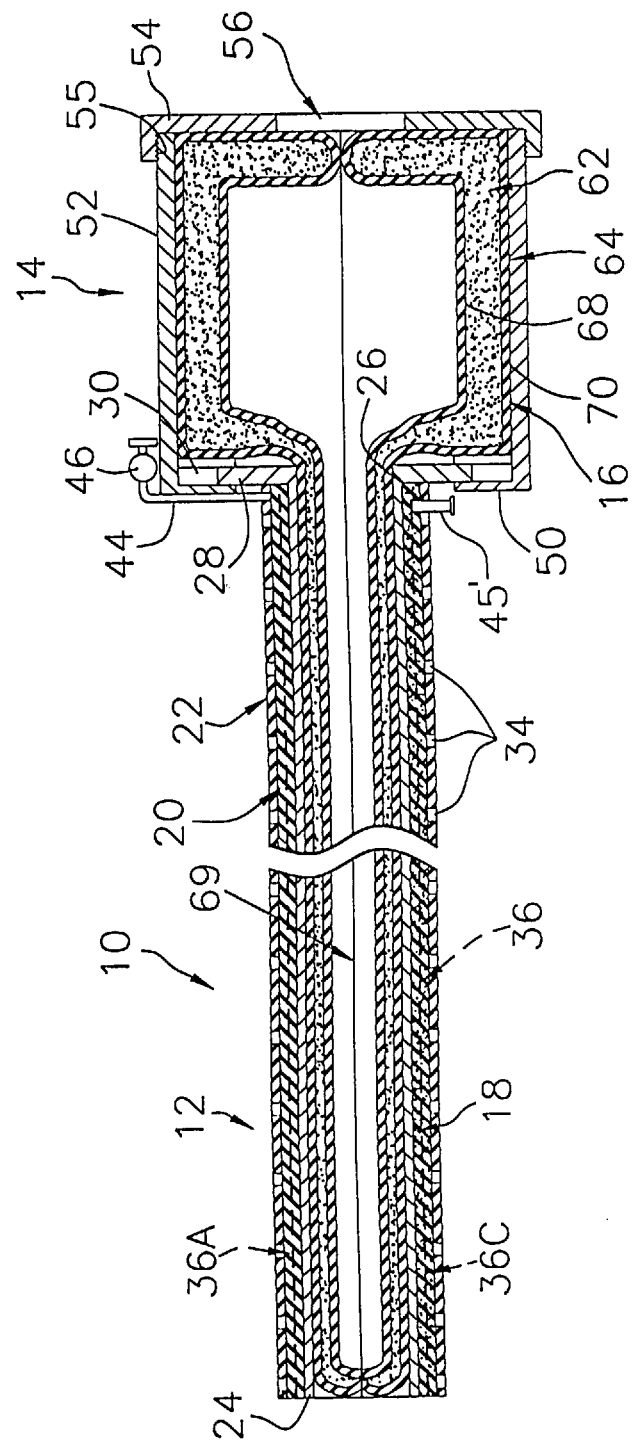

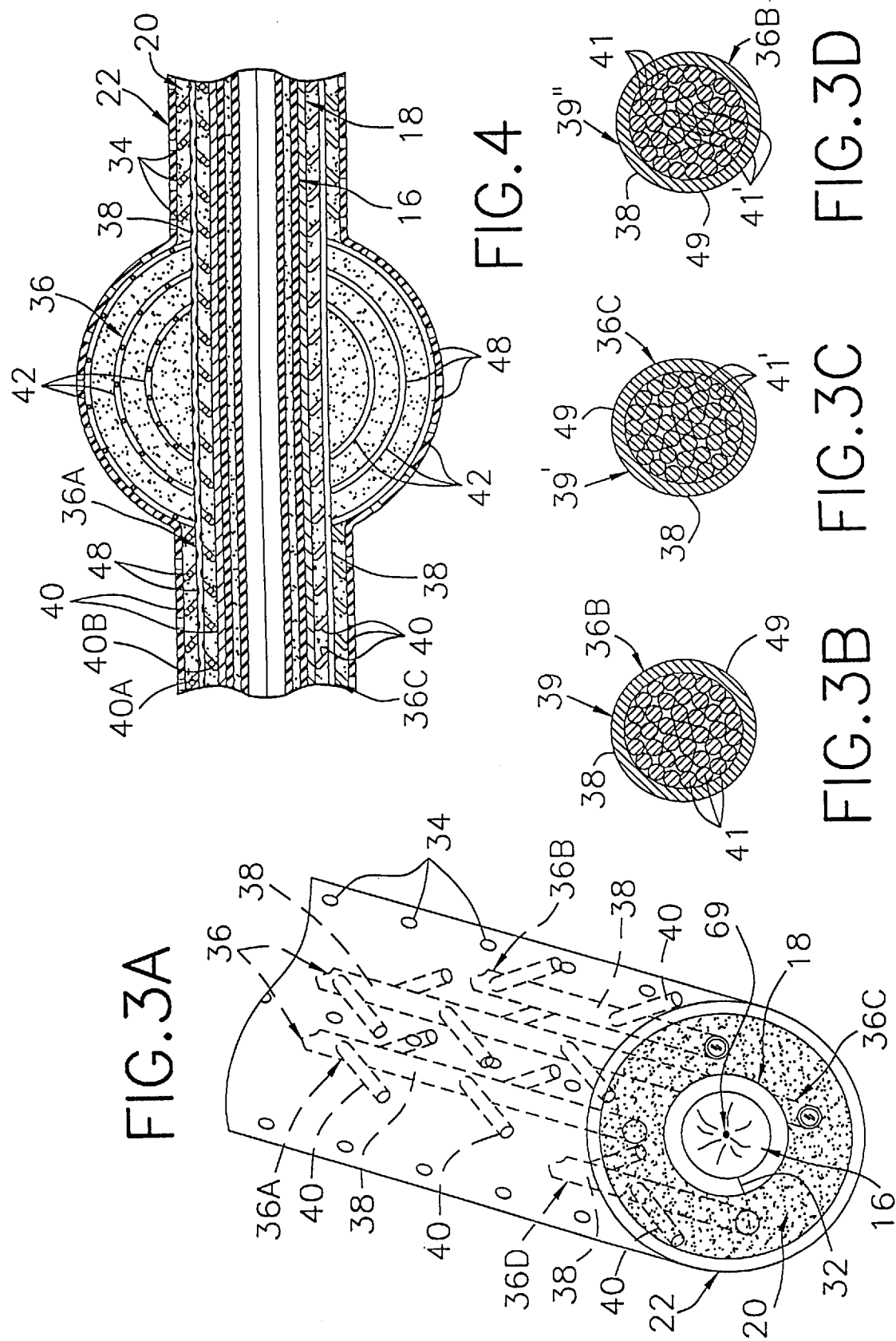

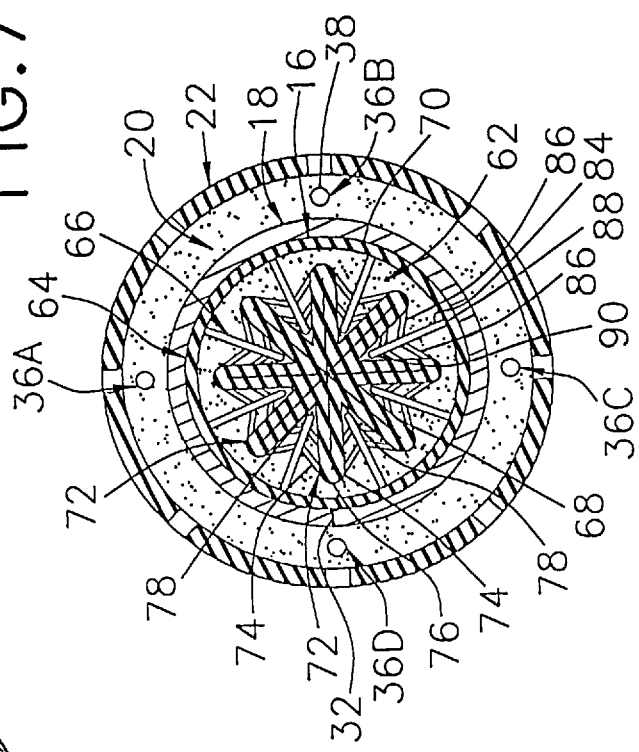
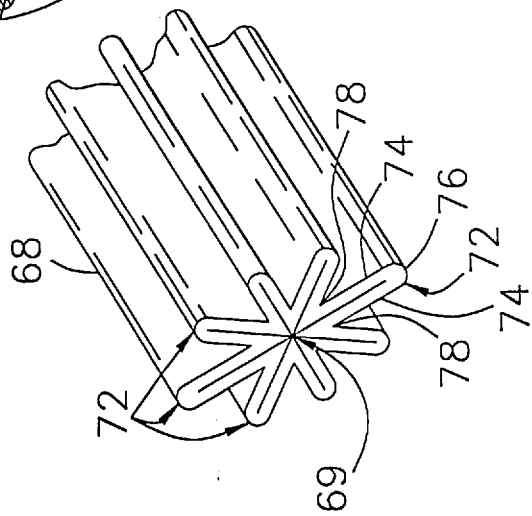

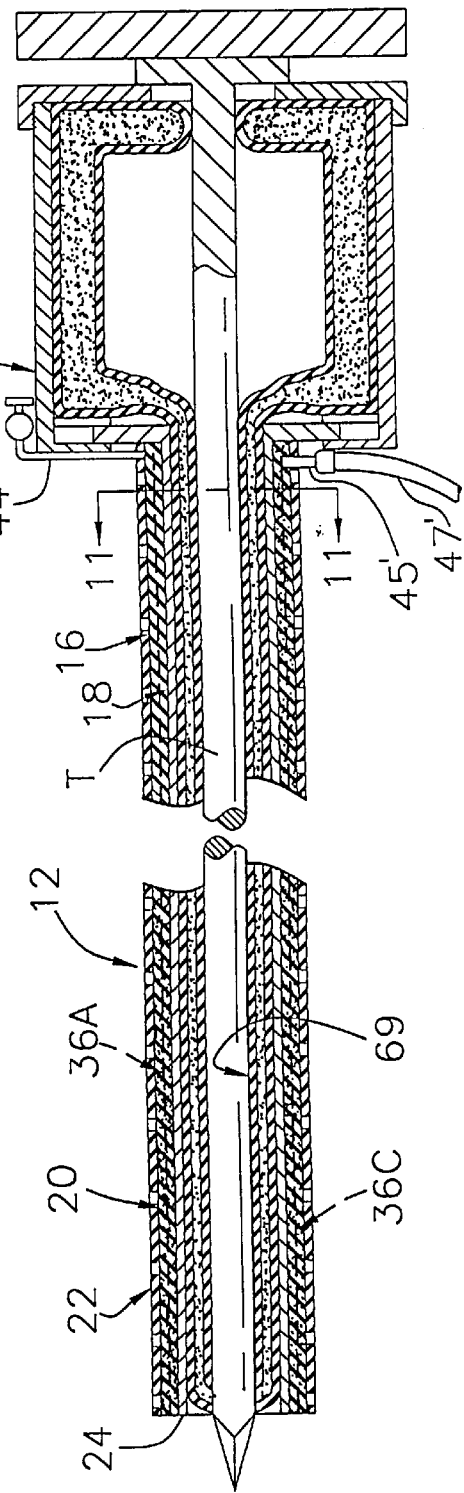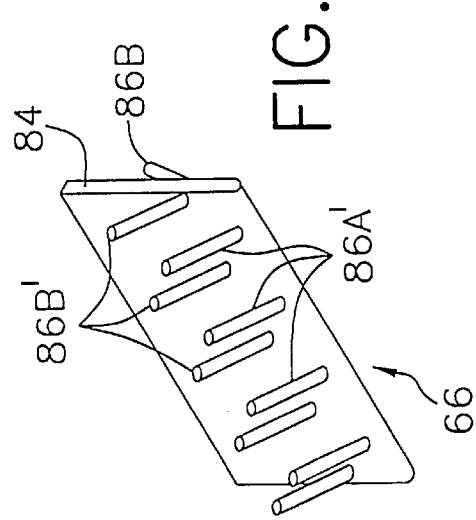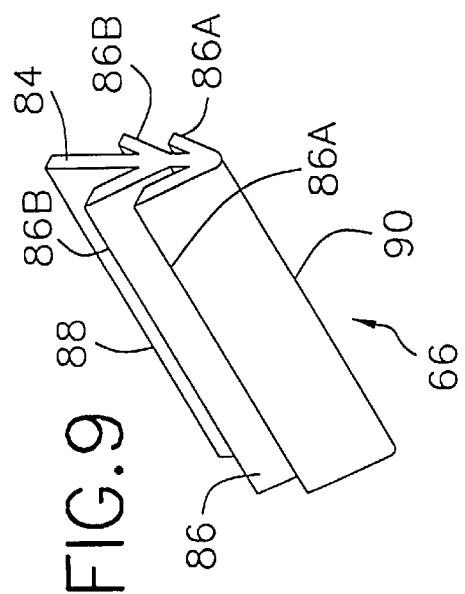

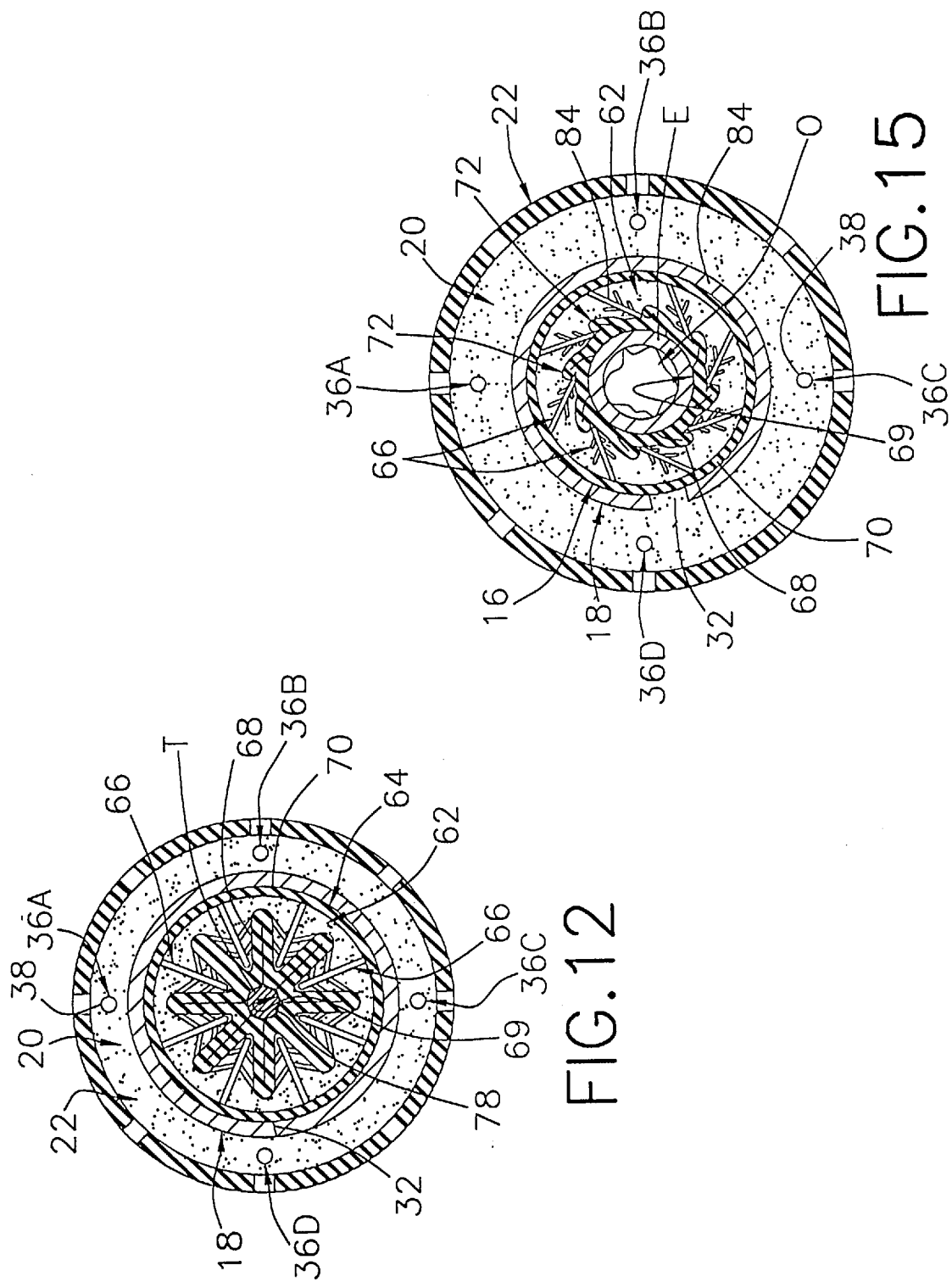

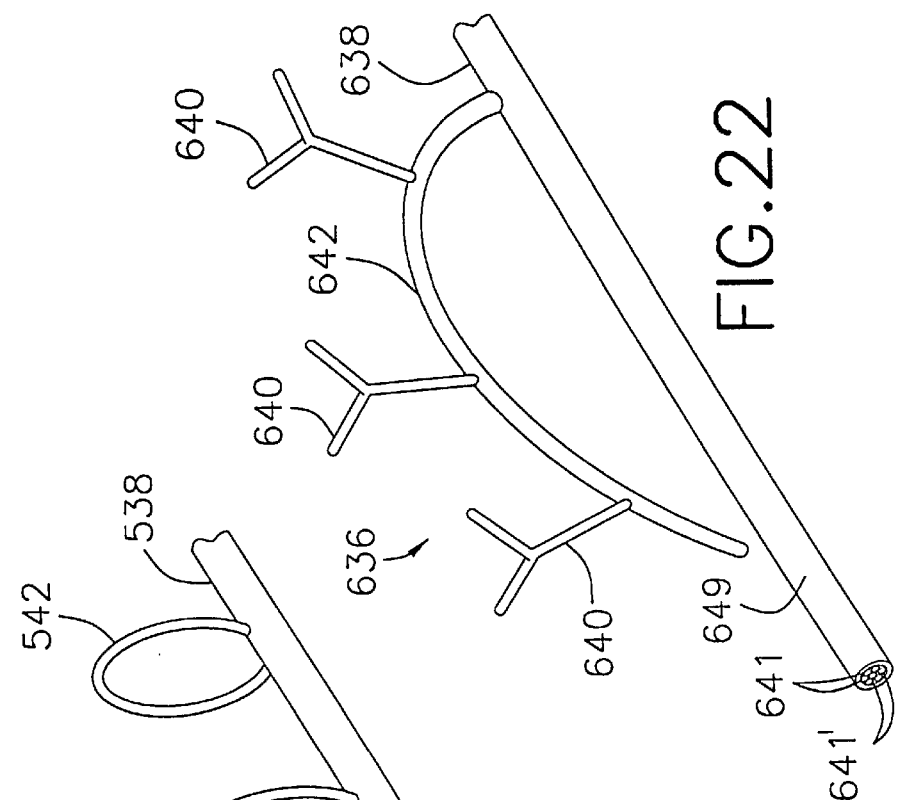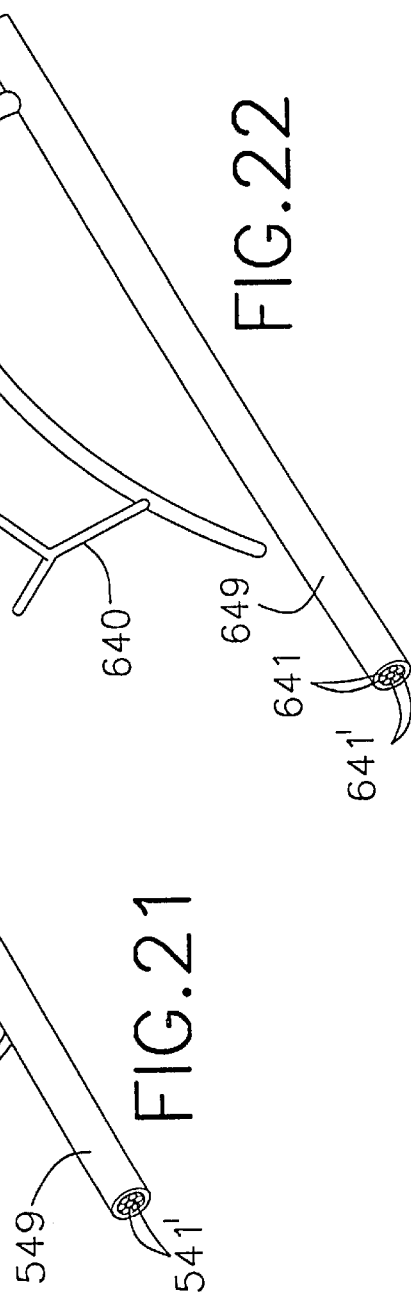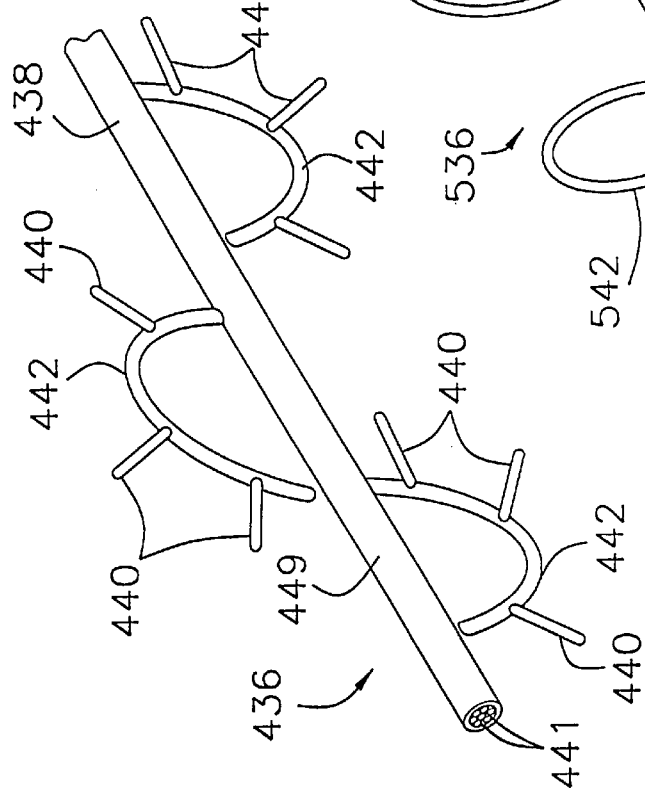

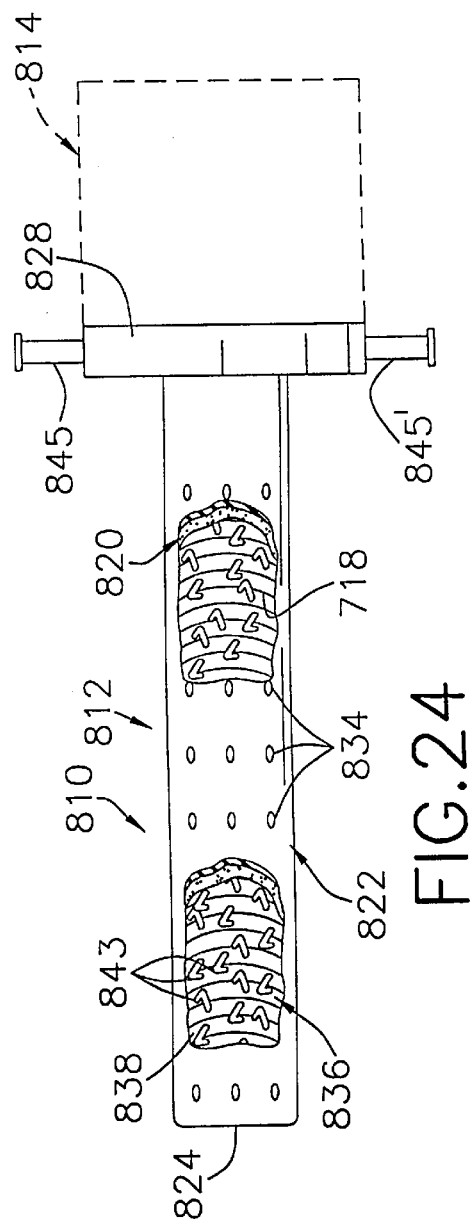
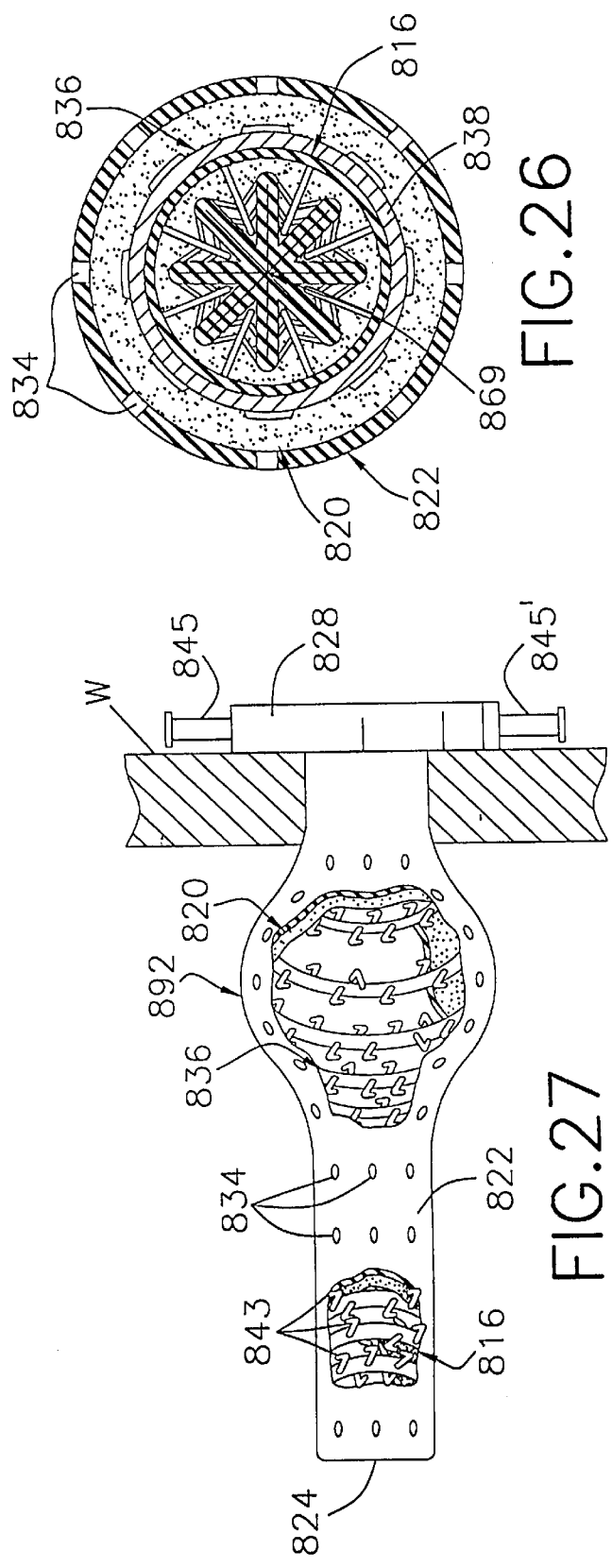

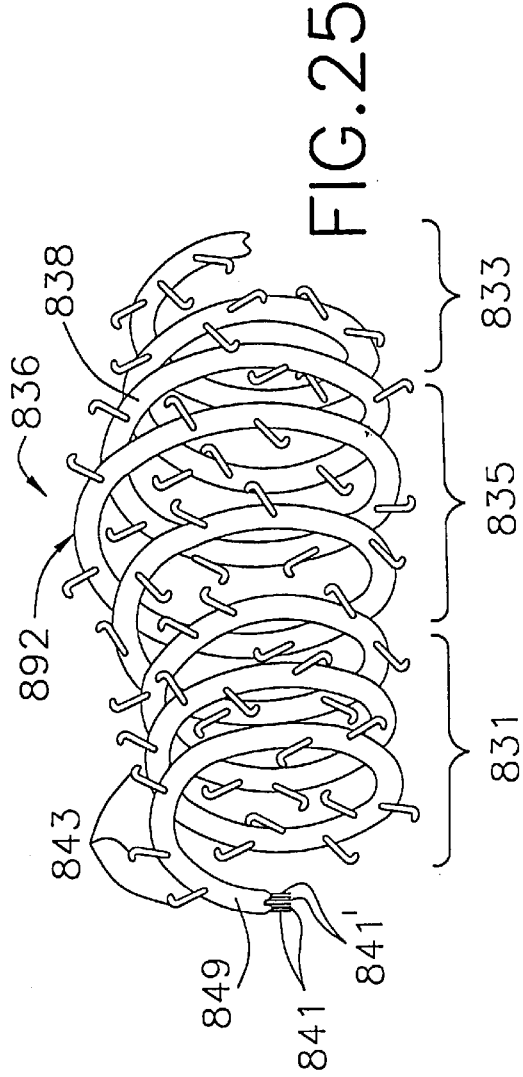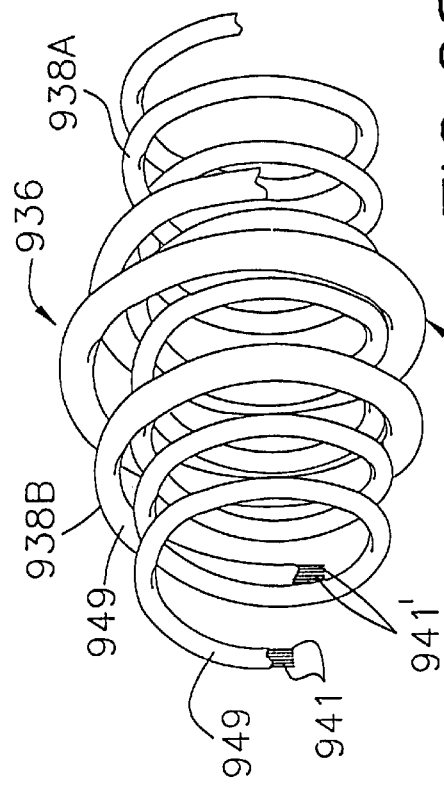

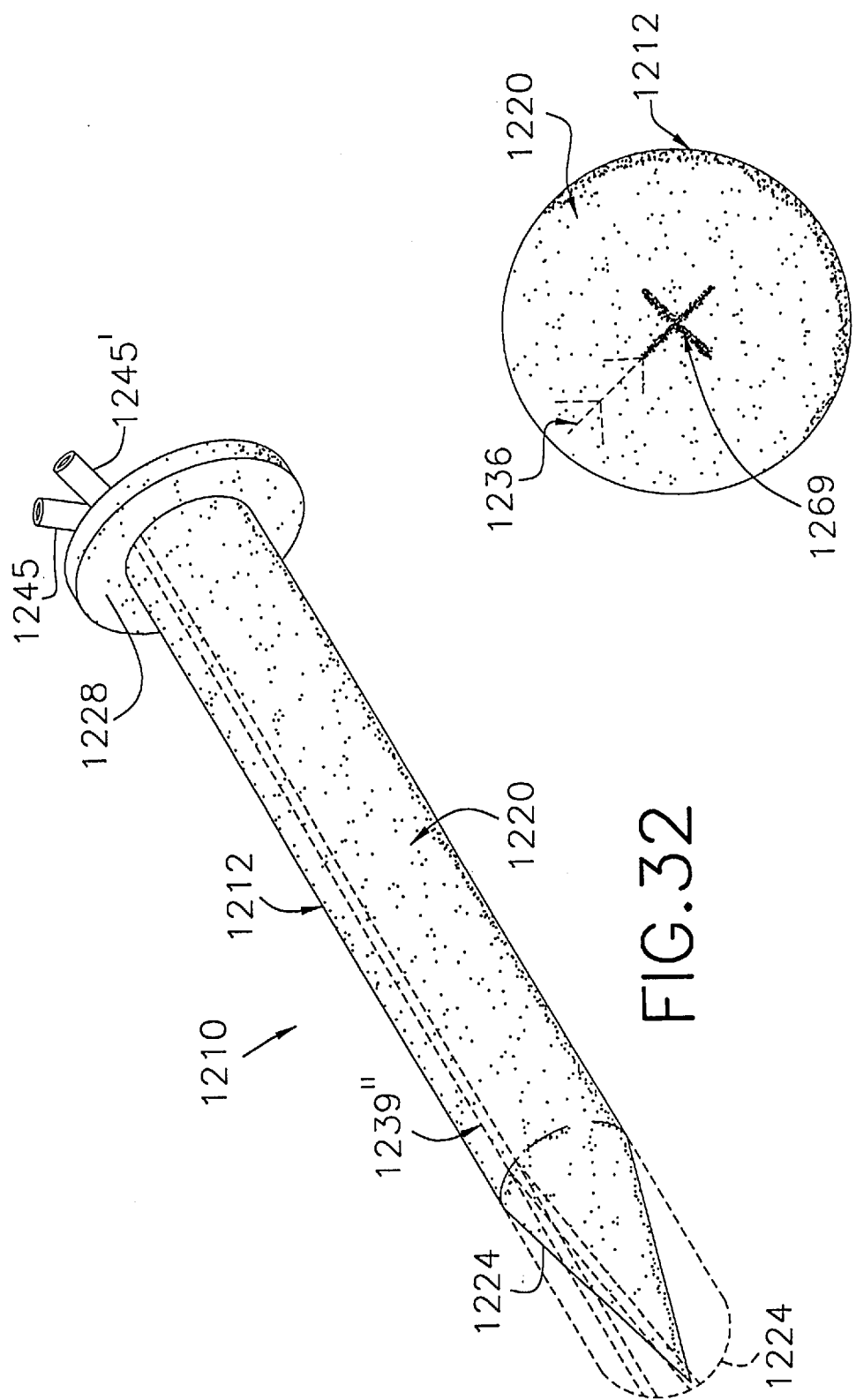

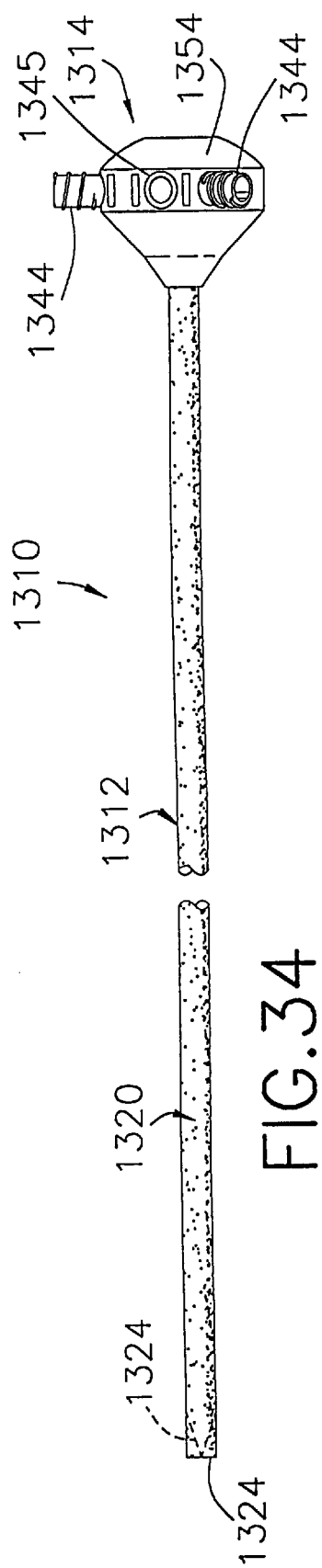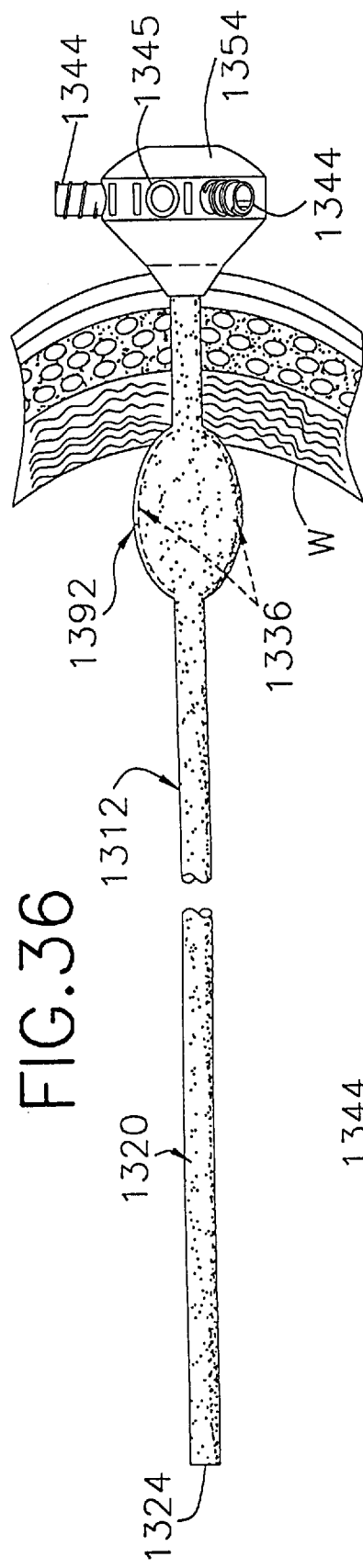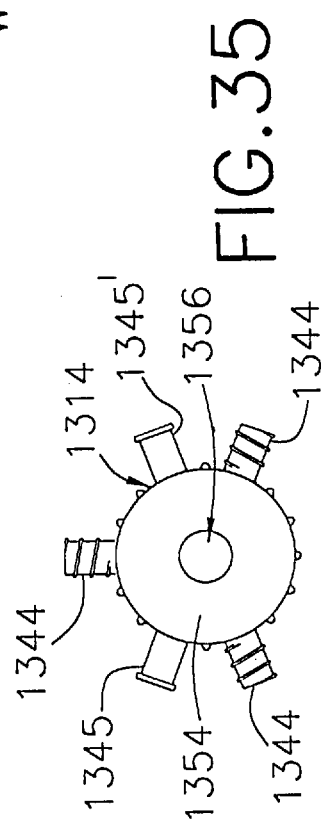

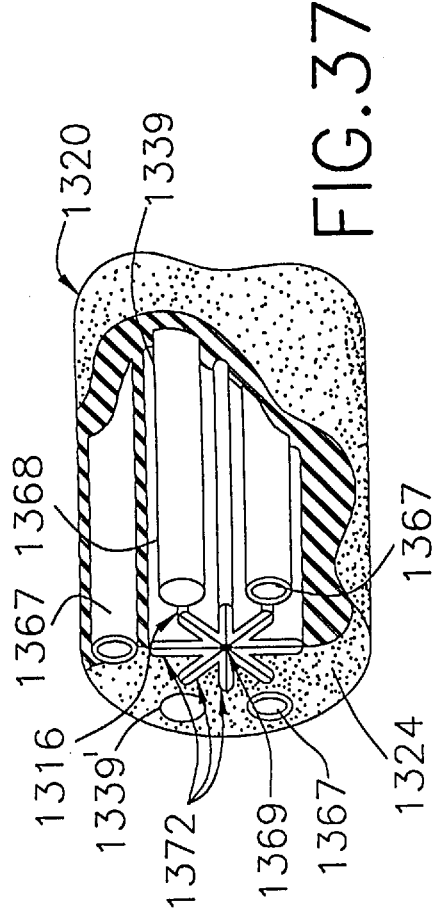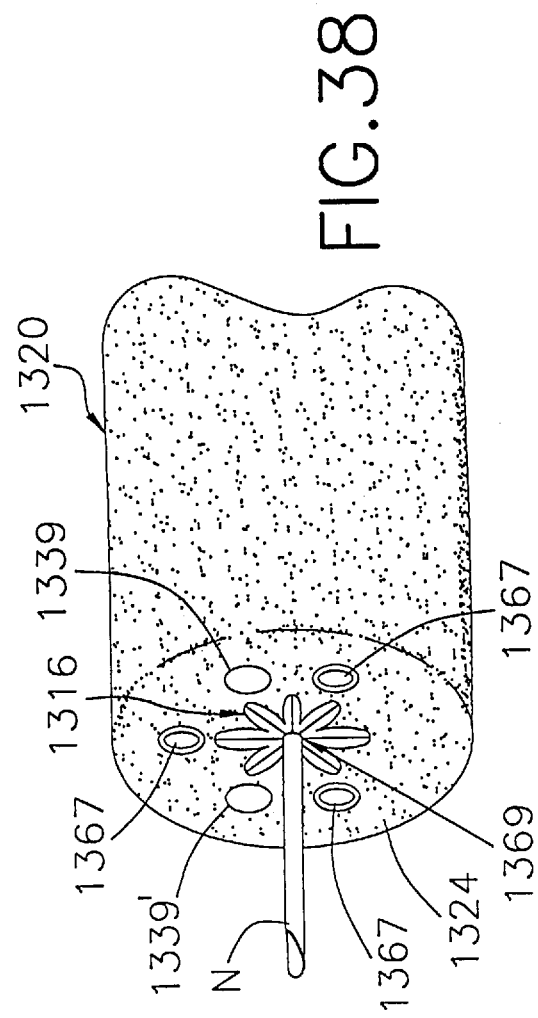

OPTICAL ENDOSCOPIC PORTALS AND METHODS OF USING THE SAME TO ESTABLISH PASSAGES THROUGH CAVITY WALLS

CROSS REFERENCE TO RELATED PATENT APPLICATIONS

This application is a continuation-in-part of pending application Ser. No. 08/651,284 filed May 22, 1996, the disclosure of which is incorporated herein by reference.

BACKGROUND OF THE INVENTION

1. Field of the Invention

The present invention pertains to endoscopic portals for establishing communication with internal sites in body cavities and, more particularly, to optical endoscopic portals having cannulas providing variable size lumens or passages through cavity walls and to methods of establishing passages through cavity walls utilizing such optical endoscopic portals.

2. Discussion of the Related Art

In endoscopic procedures, a sleeve or cannula or other structure forming a passage is normally disposed in a small size opening in a body cavity wall such that a distal end of the cannula is positioned within the body cavity and a proximal end of the cannula is disposed externally of the body cavity with a lumen or passage of the cannula providing a passage establishing communication with an internal site from externally of the body cavity. Typically, various instruments are introduced at the internal site through the lumen or passage of the cannula in order to perform diagnostic and/or surgical procedures, with the instruments many times having varying sizes in cross section. Since the lumens or passages of the cannulas are usually of fixed cross sectional size, it is necessary in a given procedure to utilize a cannula having a lumen or passage large enough to accommodate the largest size instrument to be introduced in the body cavity. Accordingly, the opening in the body cavity wall must be large enough to accommodate the cannula being used, and such opening may be larger than necessary when the instruments actually introduced through the cannula are smaller in cross sectional size than the cross sectional size of the lumen or passage. The sizes of the openings in the body cavity wall required to accommodate fixed size conventional cannulas in general necessitate performance of endoscopic procedures at hospital sites. In order to reduce trauma and shorten recovery times for patients, to expand the use of non-hospital or outpatient sites for endoscopic procedures, to permit endoscopic procedures to be performed utilizing local anesthesia, and to reduce costs, among other reasons, it would be desirable to begin an endoscopic operative procedure with as small a cannula as possible to minimize the size of the opening and to thereafter expand the cannula diametrically to non-traumatically stretch or dilate the opening to accommodate larger size instruments and/or anatomical specimens, such as organs, to be introduced in and/or withdrawn from the body. However, with endoscopic portals having fixed size cannulas, non-traumatic dilatation of the opening is not possible. Another disadvantage of presently utilized endoscopic portals is that the cannulas are not self-penetrating but require a separate penetrating member or obturator for penetrating the cavity wall.

It is important in endoscopic procedures to prevent undesired fluid flow to and from the internal site; and, accordingly, the endoscopic portals must be sealed prior to and subsequent to the introduction of instruments and while the instruments are in place. In particular, fluids such as gaseous phase carbon dioxide or nitrous oxide are normally introduced in the body for insufflation as part of the endoscopic procedure, and the escape of such fluids through the endoscopic portal should be prevented. With fixed size cannulas, the size of instruments that can be introduced through the lumen is limited since instruments having a cross sectional size larger than the fixed cross sectional size of the lumen cannot fit through the lumen; and, when instruments smaller in cross sectional size than the fixed cross sectional size of the lumen are introduced, a seal is not formed with the introduced instruments. Since the cross sectional size of the lumen must be large enough to accommodate the largest size instrument to be introduced in a procedure, there is a gap between the cannula and smaller size instruments introduced therethrough through which fluid can escape. Many endoscopic portals have valves to prevent leakage of fluid, such valves typically including one or more valve passages typically of fixed cross sectional sizes. The sizes of instruments that can be introduced in the valve passages is limited since fluids can escape past instruments having cross sectional sizes that do not correspond to the fixed cross sectional sizes of the valve passages. Universal seals having variable size passages for receiving and sealingly engaging instruments of various sizes have been proposed for endoscopic portals. Many of the universal seals proposed for endoscopic portals have various drawbacks including structural and functional complexity, the need for a separate seal housing adding to the overall length of the endoscopic portals, and failing to provide adequate support for introduced instruments.

It is also desirable in endoscopic procedures that the cannula be stabilized relative to the cavity wall to prevent backing out of the cannula from the body cavity. Although stabilizers for endoscopic portals have been proposed, most present various drawbacks due to their structural and operational complexity. In addition, conventional stabilizers typically do not afford stabilization relative to a primary cavity as well as a secondary cavity disposed in the primary cavity as would be desirable for cavity in a cavity procedures.

In endoscopic procedures, the internal operative site, typically within a body cavity, is illuminated and visualized from externally thereof with a remote viewing device, such as an endoscope or laparoscope, having a distal end positioned at the internal operative site and a proximal end positioned externally of the body cavity wall. The remote viewing device is typically introduced at the internal operative site through a sleeve or cannula extending through a small size opening in the body cavity wall, and a second sleeve or cannula extending through another small size opening in the body cavity wall is typically required for the introduction of additional instruments at the internal operative site. Accordingly, multiple openings in the cavity wall are required even though it would be more desirable or preferable to perform an endoscopic procedure utilizing a single sleeve or cannula requiring a single small size opening.

SUMMARY OF THE INVENTION

Accordingly, it is a primary object of the present invention to overcome the aforementioned disadvantages of prior art endoscopic portals.

A further object of the present invention is to provide an endoscopic cannula including an elongate member made of absorbent material, an optical element in the absorbent material for illuminating a body cavity in which a distal end of the cannula is introduced and/or for transmitting an image of the body cavity for viewing externally thereof and a passage in the cannula through which instruments are introduced in the body cavity.

The present invention has as a further object to utilize an optical element to rigidify and/or shape a flexible endoscopic cannula.

It is also an object of the present invention to provide an endoscopic cannula made of absorbent material, an optical element in the absorbent material for illuminating a body cavity in which a distal end of the cannula is introduced and/or for transmitting an image of the body cavity for viewing externally thereof and a variable size passage in the cannula through which instruments of various sizes are introduced in the body cavity in sealing relation with the cannula.

Another object of the present invention is to provide an elongate member of absorbent material configured as an obturator for penetrating a body cavity wall in a rigid dry state and configured as a cannula in a soft wet state after absorbing fluid, the elongate member carrying an optical element optically coupling distal and proximal ends of the cannula.

An additional object of the present invention is to form a cannula of an endoscopic portal as an absorbent member having a dry state prior to absorbing fluid, a wet state following absorption of fluid and a spine for rigidifying and/or shaping the absorbent member in the wet state, the spine including one or more light and/or image transmitting optical elements for illumination and/or imaging at a distal end of the cannula.

A still further object of the present invention is to form an endoscopic cannula of absorbent material having a rigid dry state prior to introduction through a small size opening in a body cavity wall, a soft wet state after absorbing fluid upon introduction of a distal end of the cannula in the body cavity and an optical element in the absorbent material optically coupling the distal end with a proximal end of the cannula.

Some of the advantages of the present invention are that the cannulas can assume predetermined external configurations and/or sizes in the wet state due to predetermined changes in the configurations and/or sizes of the absorbent members and/or the optical elements when the absorbent members are in the wet state, a single optical element can be used for both illumination and imaging, the spines or optical elements can have various extended configurations in accordance with desired external configurations and/or sizes for the cannulas when the absorbent members are in the wet state, the spines or optical elements can be maintained in contracted configurations in the dry state due to the rigidity of the dry absorbent members and return automatically to extended configurations in the wet state due to the softness or flexibility of the wet absorbent members, the optical elements can be made of conventional fiber optic elements or fiber optic cables, endoscopic operative procedures can be performed using fewer openings in body cavity walls, the overall size and length of the optical endoscopic portals can be greatly minimized since a housing or head is not necessary, the cannulas can be cut or trimmed to desired lengths prior to use, the cannulas can be used to clean areas within body cavities and/or to collect or remove anatomical specimens from body cavities, the absorbent members can be impregnated with agents useful in the procedures being performed, various substances can be supplied via the absorbent members, anesthetics can be delivered via the absorbent members such that more procedures can be performed endoscopically under local anesthesia, the absorbent members can be used to apply pressure to control bleeding, various coatings can be applied to the cannulas to control porosity, frictional characteristics and/or to protect the friable materials of the absorbent members, the cannulas can be stabilized automatically in response to absorption of fluid by the absorbent members, the absorbent members can be supplied with fluid passively and/or actively, fluids supplied by or through the cannulas can be used to wipe or clean the distal ends of the optical elements, and the optical endoscopic portals can be inexpensively manufactured for single patient use.

These and other objects, advantages and benefits are realized with the present invention as characterized in an optical endoscopic portal comprising an endoscopic cannula including an elongate member of absorbent material for being introduced through a small size opening in a body cavity wall and having a distal end for positioning in the body cavity, a proximal end for positioning externally of the body cavity and a lumen between the distal and proximal ends for receiving instruments. The elongate member has a dry state prior to introduction through the body cavity wall and a wet state after absorbing fluid upon introduction of the distal end in the body cavity. The elongate member is rigid in the dry state and is soft and flexible in the wet state. An optical element is disposed in the absorbent material and optically couples the distal and proximal ends of the cannula. The optical element transmits light from a light source external of the body cavity to illuminate the body cavity and/or transmits an image of the body cavity for viewing externally thereof. The optical element can form a spine that rigidifies and/or shapes the elongate member in the wet state. Where the optical element is a spine for shaping the elongate member, the optical element has an extended or relaxed configuration in accordance with a final external configuration and/or size desired for the cannula, is maintained in a contracted configuration when the elongate member is in the dry state due to the rigidity of the absorbent material and returns to the extended configuration when the elongate member is in the wet state due to the softness of the absorbent material. A liner or seal can be disposed in the lumen and/or in a housing for the cannula to sealingly engage instruments of various sizes introduced in the lumen. The lumen of the elongate member can itself form a variable size passage in the wet state for receiving instruments of various sizes in sealing relation. The elongate member can expand diametrically or transversely and/or longitudinally in the wet state.

A method of establishing a passage through a body cavity wall according to the present invention comprises the steps of introducing an elongate member of absorbent material in a small size opening in the body cavity wall with the elongate member in a rigid dry state, positioning a distal end of the elongate member in the body cavity and a proximal end of the elongate member externally of the body cavity with the elongate member extending longitudinally through the opening in the body cavity wall, absorbing fluid with the elongate member to place the elongate member in a soft wet state, and illuminating the body cavity and/or transmitting an image of the body cavity for viewing externally thereof with an optical element disposed in the absorbent material.

Other objects and advantages of the present invention will become apparent from the following description of the preferred embodiments taken in conjunction with the accompanying drawings wherein identical reference numbers indicate identical parts or parts providing identical function.

BRIEF DESCRIPTION OF THE DRAWINGS

FIG. 1 is a broken perspective view of an optical endoscopic portal according to the present invention.

FIG. 2 is a broken, side sectional view of the optical endoscopic portal showing the cannula in a non-expanded configuration with the absorbent member in the dry state.

FIG. 3A is a broken perspective view of a distal portion of the cannula in the expanded configuration with the absorbent member in the wet state.

FIG. 3B is a sectional view of a spine member of the spine for the cannula.

FIG. 3C is a sectional view of another spine member for the spine.

FIG. 3D is a sectional view of an alternative spine member for the spine.

FIG. 4 is a broken, side sectional view of the optical endoscopic portal showing the cannula in the expanded configuration with the spine in an extended configuration.

FIG. 7 is a sectional view of the optical endoscopic portal showing the cannula in the non-expanded configuration and the liner in a closed or initial position.

FIG. 8 is an exploded, broken perspective view of the liner.

FIG. 9 is a broken perspective view of a spine member for the liner.

FIG. 10 is a broken perspective view of a modification of a spine member for the liner.

FIG. 11 is a broken side view, partly in section, of the optical endoscopic portal showing the liner in an open or second position receiving a trocar through the cannula.

FIG. 12 is a sectional view of the optical endoscopic portal taken along line 11—11 of FIG. 11.

FIG. 15 is a sectional view of the optical endoscopic portal showing the variable size passage of the liner enlarged with a tubular expander to withdraw a body specimen through the cannula.

FIG. 20 is a broken perspective view of a modification of a spine member for use in the optical endoscopic portals according to the present invention showing the spine member in the normal extended configuration.

FIG. 21 is a broken perspective view of another modification of a spine member for use in the optical endoscopic portals according to the present invention showing the spine member in the normal extended configuration.

FIG. 22 is a broken perspective view of a further modification of a spine member for use in the optical endoscopic portals according to the present invention showing the spine member in the normal extended configuration.

FIG. 24 is a broken side view of another modification of an optical endoscopic portal showing the cannula in the non-expanded configuration.

FIG. 25 is a broken perspective view of a spine member for the optical endoscopic portal of FIG. 24 showing the spine member in the extended configuration.

FIG. 26 is a sectional view of the cannula of FIG. 24.

FIG. 27 is a broken side view of the optical endoscopic portal of FIG. 24 showing the cannula in the expanded configuration extending through a body cavity wall.

FIG. 28 is a broken perspective view of a modification of the spine member for the optical endoscopic portal of FIG. 24 showing the spine member in the extended configuration.

FIG. 32 is a perspective view of another modification of an optical endoscopic portal showing the absorbent member in the dry state.

FIG. 33 is an end view of the cannula of FIG. 32.

FIG. 34 is a broken side view of a further modification of an optical endoscopic portal showing the absorbent member in the dry state.

FIG. 35 is an end view of the optical endoscopic portal of FIG. 34.

FIG. 36 is a broken side view of the optical endoscopic portal of FIG. 34 showing the absorbent member in the wet state extending through a body cavity wall.

FIG. 37 is a broken perspective view of a distal portion of the cannula of the optical endoscopic portal of FIG. 34 showing the absorbent member in the dry state.

FIG. 38 is a broken perspective view of the distal portion of the cannula of the optical endoscopic portal of FIG. 34 showing the absorbent member in the wet state with a needle instrument introduced through the cannula.

DESCRIPTION OF THE PREFERRED EMBODIMENTS

Figure 5:
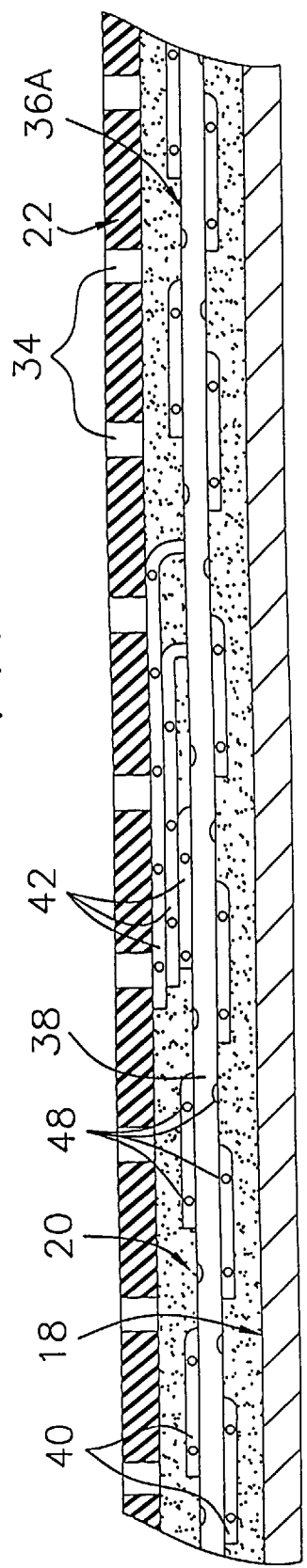
FIG. 5 is a broken, fragmentary, side sectional view of the cannula in the non-expanded configuration with the spine in a contracted configuration.

An optical endoscopic portal 10 according to the present invention is illustrated in FIGS. 1 and 2 and is similar to the endoscopic portal disclosed in prior application Ser. No. 08/651,284 filed May 22, 1996, the disclosure of which is incorporated herein by reference. Optical endoscopic portal 10 includes an elongate cannula 12, a housing or head 14 at a proximal end of cannula 12 and a liner or universal seal 16 disposed in cannula 12 and/or housing 14. Cannula 12 includes a hollow cylindrical or tubular passage defining member or sleeve 18 which, for example, can take the form of a portal sleeve or other structure providing a passage through a cavity wall, and an absorbent member 20 disposed over sleeve 18. Sleeve 18 has an open distal end 24 for being disposed in a body cavity, an open proximal end 26 for being disposed externally of the body cavity and a lumen or passage between the distal and proximal ends. Sleeve 18 terminates proximally at a transverse flange 28, shown in FIG. 2, received in a recess 30 in a forward wall of housing 14.

A longitudinal slit 32, shown in FIG. 3A, is provided in the wall of sleeve 18 extending the entire length thereof to permit expansion of sleeve 18 diametrically or in a direction transverse to a longitudinal axis of cannula 12 to increase or enlarge the cross sectional size of the lumen. Sleeve 18 is disposed in a normal, non-expanded position wherein the slit 32 is closed or substantially closed with the slit edges in contact with or close to one another, and the slit 32 is opened such that the slit edges are moved away from one another when the sleeve 18 is expanded diametrically or transversely in an expanded position by an instrument or object introduced therethrough as explained further below. To permit diametric or transverse expansion of sleeve 18, recess 30 is larger than flange 28 diametrically or in the transverse direction when the sleeve 18 is in the normal non-expanded position to provide a space into which the flange 28 is moved when the sleeve 18 is moved to the expanded position. It should be appreciated that the sleeve 18 does not have to be expandable diametrically and that the sleeve 18 can be rigid with no longitudinal slit therein.

Sleeve 18 can be made of any suitable medical grade material or materials including various rigid, semi-rigid, flexible, bendable or stretchable materials such as metals, plastics rubbers and hydrogel precursors or hydrogel forming compositions. The sleeve 18 can be made of transparent or optically clear materials. Where diametric expansion of the sleeve is desired, the sleeve can be capable of expanding diametrically or transversely due to the resilience or flexibility of the materials themselves and/or due to structure such as hinges, pivots or joints provided in or on the sleeve. Where the sleeve is made of a relatively soft material, the sleeve can be cut or trimmed to a desired length prior to use in accordance with a procedure to be performed utilizing the optical endoscopic portal. Fabricating the sleeve of a soft material has the additional advantage of minimizing trauma or damage to anatomical tissue during use.

Absorbent member 20, which comprises a body of absorbent material concentrically disposed around sleeve 18, has a rigid dry state prior to absorbing fluids and a soft wet state after absorbing fluids. The absorbent member 20 is rigid or stiff in the dry state to facilitate passage through a cavity wall. The absorbent member 20 becomes soft and pliant, malleable, resilient or flexible in the wet state after absorbing fluids, and it is desirable that the absorbent member 20 absorb fluids and soften rapidly. The absorbent member 20 in the wet state expands outwardly, diametrically, radially or in a direction transverse to a longitudinal axis of the cannula and/or longitudinally from its size in the dry state; however, the absorbent member 20 does not have to expand in the wet state. Where the absorbent member is expandable, the absorbent member can be designed for transverse or diametric expansion alone, such as by being adhesively attached to sleeve 18, and/or the absorbent member can be designed to expand longitudinally. Exemplary materials for the absorbent member include cellulose sponge, natural sponge, synthetic sponge made of a reaction product of polyvinyl alcohol and formaldehyde, hydrophilic compositions, hydrophilic cross-linked polyurethane foam, compacted gauze or cotton and hydrogel precursors or hydrogel forming compositions. The absorbent member can advantageously be made of optically clear or transparent material. The absorbent member in the dry state can carry or be impregnated with various medicaments such as antiseptics, antibiotic, coagulants, anti-coagulants and anesthetics to leach, leak or be released from the absorbent member in the wet state. Where the absorbent member 20 is expandable, it is preferred that the absorbent member expand rapidly upon absorbing fluid. The absorbent member 20 can be compressible in the wet state to facilitate withdrawal of the cannula 12 from the body. As shown in FIG. 2, the absorbent member 20 is tubular and extends the entire length of sleeve 18 distally of flange 28. The absorbent member 20 is of uniform, minimal thickness in the compressed, dry state so as not to add significantly to the external diameter or cross sectional size of the sleeve 18. The absorbent member 20 can be attached to sleeve 18, such as adhesively, or the absorbent member 20 can be unattached and free of sleeve 18.

A membrane 22 is concentrically disposed over absorbent member 20; however, a membrane disposed over the absorbent member is not required. The membrane 22 includes a thin layer of stretchable or elastic material such as Tecoflex, Teflon, Goretex or rubber, for example, concentrically disposed over absorbent member 20. Membrane 22 can be made as a tubular or hollow structure concentrically disposed over absorbent member 20, and the membrane 22 can be slightly stretched or can be relaxed when the absorbent member 20 is in the dry state. Another way in which membrane 22 can be fabricated, by way of example, is as a sheet of material wrapped around absorbent member 20 with end edges of the sheet sealed together. A plurality of small holes or perforations 34 are formed in membrane 22 to permit body fluids to contact or reach the absorbent member 20 as explained below. Absorbent member 20 and membrane 22 are distally coterminal with sleeve 18 such that distal ends of absorbent member 20 and membrane 22, respectively, are aligned with the distal end 24 of sleeve 18 and together define a distal end for cannula 12. Membrane 22 does not extend over or cover the thickness of the absorbent member 20 at the distal end thereof to facilitate absorption of body fluids by absorbent member 20 when the distal end of the cannula is disposed in a body cavity. Membrane 22 terminates proximally at a proximal end disposed distally adjacent flange 28; however, it should be appreciated that the membrane 22 can extend into or be disposed externally of the housing 14. The membrane 22 can be attached to the sleeve distal end 24 and/or to the sleeve proximal end 26 or to the housing 14. The membrane 22 can be attached to the absorbent member 20, such as adhesively, or the membrane 22 can be unattached or free of the absorbent member 20. The absorbent member 20 can be held or confined between the membrane 22 and the sleeve 18 without being attached to the membrane or the sleeve. The membrane 22 can be made of transparent or optically clear material or materials.

As best shown in FIGS. 2, 3A and 4, a spine is carried by or disposed within the body of absorbent material of absorbent member 20, and the spine for optical endoscopic portal 10 includes a plurality of spine members 36 disposed within the thickness of absorbent member 20 at spaced locations around the longitudinal axis of cannula 12. The spine for optical endoscopic portal 10 includes four spine members 36A, 36B, 36C and 36D disposed at 90° spaced locations about the cannula longitudinal axis as shown in FIG. 3A. Each spine member 36 is formed of a straight, elongate trunk 38 parallel with the cannula longitudinal axis and straight branches 40 and curved branches 42, shown in FIG. 4, extending from trunk 38. The trunks 38 of spine members 36 extend the entire or substantially the entire length of cannula 12. One or more of the spine members 36 can be tubular or hollow, and such one or more tubular or hollow spine members can be provided with holes or openings 48, as shown in FIG. 4 for spine member 36A. Distal ends of the one or more tubular or hollow spine members can terminate at the distal end 24, and such distal ends can be open to communicate with the body cavity, or the distal ends of the one or more tubular or hollow spine members can be closed. As shown in FIG. 2, a proximal end of the one or more tubular or hollow spine members is connected or coupled with one or more tubular or hollow conduits, fittings or ports, such as port 44, disposed externally adjacent the forward end of housing 14. Port 44, which is flexible, communicates with or carries a valve 46, such as a stop cock, for controlling fluid flow therethrough. In optical endoscopic portal 10, the port 44 is coupled with hollow spine member 36A and is connectible with a source of fluid and/or suction or vacuum. Where the hollow spine member 36A is provided without holes 48 but has an open distal end communicating with the body cavity, fluid, such as insufflation gas can be introduced in the body cavity and/or fluids and/or tissue can be aspirated or evacuated from the body cavity via the spine 36A and port 44. Where the spine member 36A is provided with holes 48, fluid can be supplied to the absorbent member 20 and/or fluid can be aspirated from the absorbent member 20 via spine member 36A and port 44. Accordingly, in addition or alternative to supplying fluid to the absorbent member 20 passively via contact with body fluids, the absorbent member 20 can be supplied with fluid actively, via one or more spine members, from externally of the body cavity. Where the absorbent member is actively supplied with fluid, the membrane 22 can be provided without holes 34. It should be appreciated that a valve 46 can be provided for each port 44, with the valves 46 being operable to selectively open and close the ports 44, respectively, to control fluid flow therethrough. It should also be appreciated that a combination of spine members can be provided in absorbent member 20 to define supply and/or evacuation channels through the absorbent member for performing different functions, i.e. forced or active supply of fluid to absorbent member 20, evacuation of fluid from absorbent member 20, supply of substances, including medicaments and therapeutic agents, to the body cavity and evacuation of substances from the body cavity. Where the port 44 extends through a hole or opening in the membrane 22, a seal can be provided in the optical endoscopic portal 10 to prevent leakage of fluid from the absorbent member through the hole or opening in membrane 22 through which the port 44 extends.

At least one of the spine members 36 is an optical spine member including or consists of one or more optical elements optically coupling the distal and proximal ends of the cannula. In optical endoscopic portal 10, spine member 36B is a light transmitting spine member including one or more light transmitting optical elements for transmitting light from a light source to illuminate the body cavity. As shown in FIG. 3B, at least the trunk 38 of spine member 36B is formed as a light transmitting optical element 39 including a plurality or bundle of light transmitting fiber optic filaments or fibers 41 closely arranged in an outer sheath 41 or cladding 49. The light transmitting optical element 39 terminates distally at or adjacent the distal end of absorbent member 20 and is proximally coupled with a light coupler 45, shown in FIG. 1, disposed externally adjacent the forward end of housing 14 protruding through a hole in membrane 22. The light coupler 45 is selectively connectible with and disconnectible from a fiber optic light guide or cable 47 connected with a light source as shown in FIG. 1. Light from the light source is transmitted via the light guide 47 to the optical spine member 36B and is transmitted via the optical spine member 36B to provide illumination at the distal end of the optical endoscopic portal 10. If desired, a seal can be provided in the optical endoscopic portal 10 to prevent leakage of fluid from the absorbent member through the hole in membrane 22 receiving the light coupler 45.

Alternatively or in addition to light transmitting spine member 36B, at least one of the spine members 36 is an optical spine member including or consisting of one or more image transmitting optical elements for receiving and transmitting an image of the body cavity for viewing externally thereof. In optical endoscopic portal 10, spine member 36C is an image transmitting spine member including one or more image transmitting optical elements. At least the trunk 38 of spine member 36C is formed as an image transmitting optical element 39' including a plurality or bundle of image transmitting fiber optic filaments or fibers 41', closely arranged in an outer sheath or cladding 49 as shown in FIG. 3C. The image transmitting optical element 39' terminates distally at or adjacent the distal end of absorbent member 20 and is coupled proximally with an image coupler 45', shown in FIGS. 1 and 2, disposed externally adjacent the forward end of housing 14 and passing through a hole in membrane 22. The image coupler 45' is selectively connectible with and disconnectible from a fiber optic image guide or cable 47' connected to a viewing device such as a video monitor or eyepiece. Accordingly, the body cavity can be visualized remotely, from externally thereof, via the viewing device, which displays images of the body cavity received and transmitted by the optical spine member 36C. If desired, a seal can be provided in the optical endoscopic portal 10 to prevent leakage of fluid from the absorbent member through the hole in membrane 22 through which the image guide 47' passes. It should be appreciated that the viewing device can be coupled directly to the image transmitting spine member 36C without the need for image guide 47'.

As shown in FIG. 1, the light guide 47 and the image guide 47' can be attached or connected to one another to form a harness. It should be appreciated that both the trunks and branches of the spine members can be formed as light and/or image transmitting optical elements. The light and/or image transmitting filaments or fibers can be disposed in the absorbent member without an outer sheath or sheaths, and the light and/or image transmitting optical elements can be fiber optic cables. It should be further appreciated that a single spine member can be both a light transmitting and image transmitting spine member and that a single optical element can be both a light and image transmitting optical element. For example, FIG. 3D shows the trunk 38 of spine member 36B formed as a light and image transmitting optical element 39" including a plurality of light transmitting fibers 41 and a plurality of image transmitting fibers 41" disposed in outer sheath 49, the light and image transmitting fibers being coupled with light and image couplers, respectively. It should be appreciated that the light transmitting and/or image transmitting optical elements can include various lenses, prisms, mirrors, focusing systems and/or illumination systems. The sheaths 49 can be made of various protective materials including fluid impervious materials.

Each spine member 36 has a normal, extended configuration shown in FIGS. 3A and 4 wherein branches 40 extend from trunk 38 at an acute angle to the distal direction, the branches 40 having first ends merging or connected with trunk 38 and having second, free or unattached ends. The straight branches 40 are arranged in pairs along trunk 38 distally and proximally of curved branches 42, one branch 40A of each pair extending from trunk 38 in the direction of membrane 22 and the other branch 40B of each pair extending from trunk 38 in the direction of sleeve 18 with the branches 40A and 40B of each pair being spaced from one another longitudinally along trunk 38. Branches 40B extend along the portion of the length of trunk 38 corresponding to curved branches 42 while branches 40A do not. The branches 40 are capable of bending, flexing or pivoting inwardly toward trunk 38 to move the free ends thereof in the direction of trunk 38.

Branches 42 curve outwardly from trunk 38 in the normal, extended configuration and have first ends merging or connected with trunk 38 and second, free or unattached ends. Three branches of similar curvature and of increasing length are provided on each spine member 36 with the branches being arranged in nesting fashion from shortest to longest with the shortest branch disposed closest to trunk 38, the longest branch disposed furthest away from trunk 38 and the next longest branch disposed between the longest and shortest branches. Branches 42 and trunks 38 of spine members 36 disposed at 180° spaced locations are coplanar with one another, and with the cannula longitudinal axis, and the branches 42 curve outwardly from trunks 38 in a direction away from the cannula longitudinal axis in the extended configuration. Accordingly, the branches 42 and trunks 38 of the first pair of spine members 36A and 36C disposed at 180° spaced locations are disposed in a first plane containing the cannula longitudinal axis, and the branches 42 and trunks 38 of the second pair of spine members 36B and 36D disposed at 180° spaced locations are disposed in a second plane containing the cannula longitudinal axis and bisecting the first plane. The branches 42 of a spine member are parallel to one another in the extended configuration. Branches 42 are capable of being deformed, compressed or flattened toward trunks 38.

The spine members 36 are movable from the normal extended configuration to a constrained, collapsed or contracted configuration wherein branches 40 and 42 are disposed close to or in contact with trunks 38 in substantial alignment therewith as shown in FIG. 5 for spine member 36A. In the contracted configuration, branches 40 are pivoted about their first ends toward the corresponding trunk 38 such that the branches 40 lie flat or substantially flat against the corresponding trunk 38. Branches 42 of each spine member are compressed or flattened to lie parallel or substantially parallel with and close to the corresponding trunk 38 with the branches 42 arranged in overlapping fashion. Accordingly, in the contracted configuration, the spine members 36 fit or are contained within the thickness of the absorbent member 20 in the dry state. Due to the stiffness and rigidity of the absorbent member 20 in the dry state, the spine members 36 are maintained or constrained by the absorbent member in the dry state to be disposed in the contracted configuration. The spine members 36 have resilience and/or shape memory, causing the spine members to return automatically to the normal, extended configuration when the absorbent member 20 becomes soft, flexible and pliant in the wet state. The spine members 36 are shown disposed within or embedded in the layer of absorbent member 20; however, the spine members can be disposed externally of the absorbent member partly or entirely, such as being interposed between the absorbent member 20 and the membrane 22 or between the absorbent member 20 and the sleeve 18. Any number of spine members 36 can be provided to obtain a desired external configuration for cannula 12 in the wet state. The spine can include individual, separate spine members as shown for optical endoscopic portal 10, or the spine can be designed as an integral, unitary structure having a single spine member or interconnected spine members. The spine can terminate externally or outside of housing 14 or the spine can terminate within or extend through the housing 14.

The materials selected for particular spine members will depend on whether the spine members are to be hollow or solid and whether or not the spine members are to be optical elements. For spine members that are optical elements, such as spine members 36B and 36C, the sheaths 41 can be made of materials having shape memory or spring-like properties and the filaments within the sheaths can be flexible to move with the sheaths when the spine members are moved between the contracted and extended positions. Where the filaments extend only through the trunks of the spine members and the trunks remain in the same configuration when the spine members are in the contracted and extended positions, as is the case for spine members 36B and 36C, the trunks of the spine members need not be made of flexible, spring-like materials but can be made of rigid materials. In the latter case, the branches of the spine members are made of flexible materials or materials having shape memory or spring-like properties and are attached or joined to the rigid trunks. The trunks and branches of the spine members can be made integrally, unitarily as one piece or as separate pieces or parts.

Housing 14 can be made of any suitable materials such as plastics and metals and can have any desirable configuration to facilitate grasping including a cylindrical configuration as shown in FIG. 1. As shown in FIG. 2, housing 14 includes transverse forward wall 50 having recess 30 therein receiving flange 28, a cylindrical body 52 extending proximally from forward wall 50 and an end cap 54 removably mounted on an open proximal end of cylindrical body 52. End cap 54 can be removably mounted on cylindrical body 52 in many various ways including a threaded connection as shown at 55 in FIG. 2. End cap 54 defines a transverse rearward wall of housing 14, the rearward wall 54 being parallel to forward wall 50 and having an opening 56 therein longitudinally or axially aligned with the lumen of sleeve 18. Opening 56 is of a size large enough to accommodate the cross sectional size of the largest instrument or object to be introduced and/or withdrawn through the optical endoscopic portal 10 for a specific procedure allowing the largest size instrument or object as well as smaller size instruments or objects to pass therethrough. Since the end cap 54 is removable from cylindrical body 52, the end cap 54 can be removed and replaced with another, different end cap having a larger opening to accommodate larger size instruments or objects, or the end cap 54 can be replaced with an end cap having an opening corresponding in size to the cross sectional size of a particular instrument.

Figure 6:
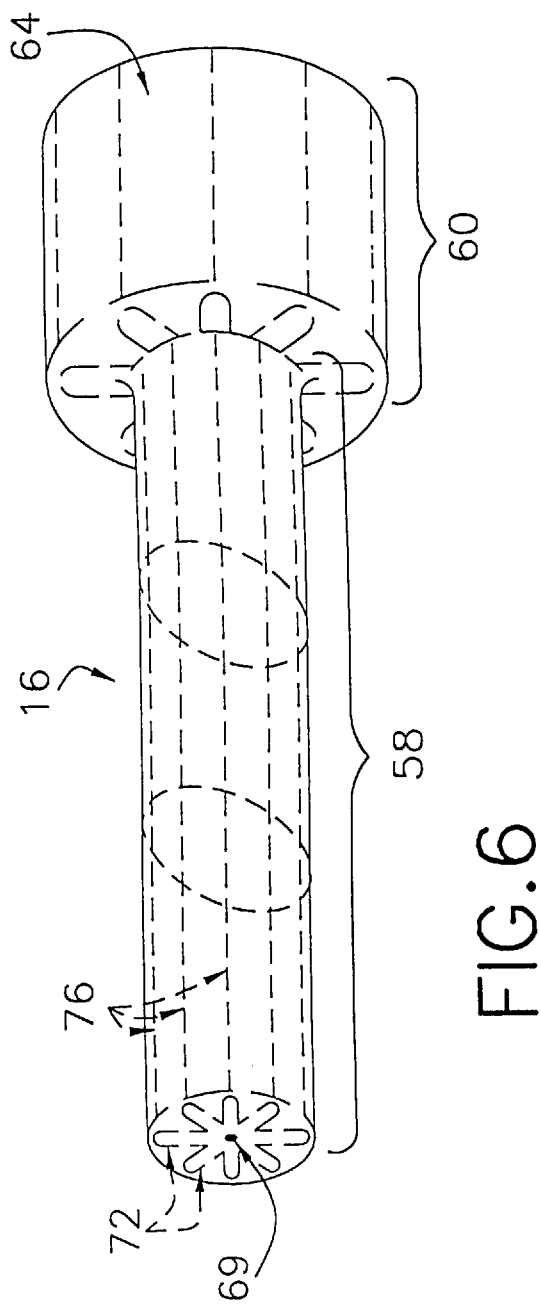
FIG. 6 is a perspective view of a liner for the optical endoscopic portal.

As shown in FIG. 6, universal seal or liner 16 includes a cannula portion 58 disposed within cannula 12 and a housing or head portion 60 disposed in the interior of housing 14.

The cannula portion 58 has an external cross sectional size to fill the lumen of sleeve 18, and the housing portion 60 has an external cross sectional size, greater than the external cross sectional size of cannula portion 58, to fill the cross sectional interior of cylindrical body 52. The cannula portion 58 has a length to extend the entire or substantially the entire length of sleeve 18, and the housing portion 60 has a length to fill the interior of housing 14 longitudinally between forward wall 50 and rearward wall 54. As best shown in FIG. 7, seal 16 is made up of a compressible member 62, a membrane 64 encapsulating compressible member 62 and a spine including one or more spine members 66 within compressible member 62, the seal 16 having a plurality of spine members 66. Membrane 64 includes an inner membrane section 68 disposed within a longitudinal passage of the compressible member and defining a variable size passage 69 and an outer membrane section 70 disposed around inner membrane section 68 and compressible member 62. The inner and outer membrane sections are connected to one another to define a closed or sealed envelope containing compressible member 62, which is disposed between the inner membrane section 68 and the outer membrane section 70. As shown in FIGS. 7 and 8, FIG. 7 showing trunks 38 without branches 40 and 42 and FIG. 8 showing the inner membrane section 68 without the outer membrane section 70, the inner membrane section 68 is pleated or folded about a longitudinal axis of seal 16, coaxial with the cannula longitudinal axis, to define a plurality of interconnected, radial pleats or folds 72 about variable size passage 69. Inner membrane section 68 has a sphincter configuration with each pleat 72 defined by two juxtaposed walls 74 extending radially to the longitudinal axis of seal 16, which is coaxial with variable size passage 69, an outer bend 76 joining walls 74 to one another and an inner bend 78 for each wall 74, the inner bends 78 joining walls 74, respectively, to the walls of adjacent pleats, respectively. As shown in dotted lines in FIG. 6, pleats 72 extend lengthwise from a distal end of seal 16 to a proximal end thereof, with outer bends 76 extending longitudinally through compressible member 62. Along the cannula portion 58, each pleat 72 extends a first radial distance from the longitudinal axis of seal 16; and, along the housing portion 60, each pleat 72 extends a second radial distance, greater than the first radial distance, from the longitudinal axis of seal 16. However, it should be appreciated that the distance that the pleats extend radially from the seal longitudinal axis can be the same along the cannula portion 58 and the housing portion 60. The membrane 64 can be made of various medical grade materials as described for membrane 22, and the membrane 64 can be transparent or optically clear. The outer membrane section 70 is stretchable; however, the inner membrane section 68 can be non-stretchable or stretchable. Preferably, at least the inner membrane section 68 is made of a slippery, tearing resistant or non-breakable material.

Compressible member 62 disposed within membrane 64 comprises a body of compressible material filling the space between the inner membrane section 68 and the outer membrane section 70 and between adjacent pleats 72 such that the walls 74 of each pleat 72 are in contact with one another and the inner bends 78 are urged inwardly toward one another in the direction of the seal longitudinal axis. Compressible member 62 and/or spine members 66 biases the seal 16 to a normal closed or initial position wherein the inner bends are biased close to or in contact with one another along variable size passage 69 such that the variable size passage 69 through seal 16 is normally closed or is of a first cross sectional size. In the case of seal 16, the variable size passage 69 is closed in the closed or initial position with inner bends 78 in contact with one another as shown in FIG. 7. Seal 16 fills sleeve 18 and housing 14 such that outer membrane section 70 is in contact with the internal surfaces of sleeve 18 and housing 14. The distal end of seal 16 is aligned with or adjacent the distal end 24 of sleeve 18, and a proximal end of seal 16 abuts end cap 54 with variable size passage 69 communicating with opening 56 of end cap 54. The body of compressible material can include various materials such as sponge, fluid, foam and gel, the compressible member 62 being made of compressible sponge. It should be appreciated that the compressible member 62 does not have to be encapsulated in a membrane and, therefore, that the seal 16 can be made up of a compressible member without a membrane. The compressible member can be made of an absorbent material, similar to the absorbent materials for absorbent member 20, and the compressible member can be supplied with fluid prior to or during use to soften the compression. A fluid supply conduit can be connected with the compressible member for supplying fluid to the compressible member. The compressible member can be made of a transparent or optically clear material.

FIG. 8 illustrates schematically one way of forming seal 16 having a membrane, only the inner membrane section 68 being shown. Compressible member 62, only a portion of which is shown, has a first cylindrical section, shown in FIG. 8, corresponding to cannula portion 58 and a second cylindrical section (not shown), larger in cross sectional size than the first cylindrical section, corresponding to housing portion 60. The first and second cylindrical sections can be integrally, unitarily formed. A recess 80 extends longitudinally through the compressible member 62 and has a multi-lobed configuration in cross section defining a radially extending recess lobe 82 for each pleat 72. Membrane 64 is disposed in recess 80 with each pleat 72 disposed in a corresponding recess lobe 82. A portion of membrane 64 extending externally from compressible member 62 is folded back over the compressible member 62 to form outer membrane section 70. The inner and outer membrane sections 68 and 70 are joined to one another at their ends, such as adhesively or via heat sealing or bonding. Spine members 66 are not shown in FIG. 8; however, it should be appreciated that the spine members 66 can be disposed within the compressible member 62 prior to assembly of compressible member 62 with membrane 64. The seal 16 can also be formed by various molding and extrusion processes.

Spine members 66, best illustrated in FIGS. 7 and 9, each include a straight trunk 84 and straight branches 86 extending angularly from trunk 84. Each trunk 84 includes an elongate planar strip of material of uniform thickness and having parallel outer and inner edges 88 and 90, respectively, extending the length of trunk 84. Each spine member 66 is arranged within compressible member 62 to be disposed between two adjacent pleats 72 with the trunk 84 thereof disposed in a plane radial to the seal longitudinal axis. Each trunk 84 is disposed mid-way between two adjacent pleats 72 with inner edge 90 disposed closer to the seal longitudinal axis than outer edge 88. The branches 86 include a pair of short branches 86A and a pair of long branches 86B extending angularly outwardly from trunk 84 toward the adjacent pleats 72. Branches 86A are angled symmetrically from opposite sides of trunk 84 and have first ends attached to trunk 84 at inner edge 90 with the branches 86A extending angularly outwardly from trunk 84 in the direction of outer edge 88 to terminate at unattached second ends. Branches 86B are angled symmetrically from opposite sides of trunk 84 and have first ends attached to trunk 84 between outer edge 88 and inner edge 90 with the branches 86B extending angularly outwardly from trunk 84 in the same direction as branches 86A such that the branches 86A and 86B disposed on the same side of trunk 84 are parallel with one another. Each branch 86 is made as an elongate, planar strip of material of uniform thickness joined along one edge to trunk 84 and extending the entire length thereof. Branches 86 are shown contacting membrane 64 in FIG. 7; however, the compressible member 62 can be disposed around the spine members 66 such that no parts of the spine members 66 contact membrane 64.

Spine members 66 add stiffness or rigidity to the compressible member 62 to maintain the normal closed or initial position for seal 16. It should be appreciated, however, that where the compressible member 62 has sufficient rigidity, stiffness, or strength, a spine is not necessary. The spine members 66 can be disposed within the compressible member 62 in many various ways including being embedded in the compressible member, being disposed in preformed recesses of the compressible member and via molding and extrusion processes. If necessary, the spine members 66 can be attached, such as adhesively, to the compressible member. The spine members 66 extend the entire or substantially the entire length of the universal seal 16; and, accordingly, each spine member extends longitudinally along both the cannula portion 58 and the housing portion 60 in which case the spine members can be bent or angled at the junction of the cannula portion 58 with the housing portion 60. Alternatively, each spine member 66 can be discontinuous and made of separate, unattached segments. The spine members can be made of flexible, resilient materials having spring-like properties to bend, deform, buckle or "give" when the seal 16 is moved to an open or second position to accommodate an object introduced therethrough or the spine members can be made of rigid materials and pivoted, deflected or moved by an object introduced through seal 16 to accommodate the object in variable size passage 69. As shown in FIG. 10, the spine members 66 can be designed with individual branch segments 86A' and 86B' longitudinally spaced from one another along trunk 84 with the branch segments 86A' being staggered with respect to the branch segments 86B'. One or more of the spine members 66 can be formed in a manner similar to light transmitting spine member 36B and/or image transmitting spine member 36C to provide a light transmitting and/or image transmitting spine member or members in seal 16. Where one or more of the spine members 66 are a light transmitting and/or image transmitting spine member or members, the distal ends of such one or more spine members can protrude through the membrane 64 at the distal end of the optical endoscopic portal 10; however, where the compressible member 62 and the membrane 64 are optically clear or transparent, optical elements forming one or more of the spine members 66 do not have to protrude externally of membrane 64. The liner can be in the form of a valve as disclosed in U.S. Pat. No. 5,389,080, No. 5,429,609 and No. 5,441,486, the disclosures of which are incorporated herein by reference, and which also disclose materials suitable for construction of seal 16.

Prior to use, absorbent member 20 is in the dry state with spine members 36 maintained in the contracted configuration. Sleeve 18 is in the normal non-expanded position with slit 32 closed. Accordingly, cannula 12 is rigid and has a non-expanded configuration presenting a smooth, uniform profile facilitating passage through a body cavity wall with an initial external diameter or cross section that is uniform along the length of the cannula distally of housing 14. Universal seal 16 is in the closed or initial position with inner bends 78 biased into contact with one another to close variable size passage 69.

When it is desired to use optical endoscopic portal 10 to provide a passage through a body cavity wall, a penetrating member or obturator, such as a trocar T, is inserted through universal seal 16 as shown in FIG. 11 causing the variable size passage 69 to open or enlarge to receive the trocar T. Accordingly, universal seal 16 will be in an open or second position with the cross sectional size of passage 69 enlarged to receive the trocar T as shown in FIG. 12, which does not show branches 40 and 42 of trunks 38. The seal 16 exerts a compressive sealing force on the trocar T in the manner of a sphincter while the sleeve 18 remains in the normal non-expanded position with slit 32 closed. The compressible member 62 will be compressed and the spine members 66 will be deflected due to introduction of trocar T in variable size passage 69, and the compressible member 62 and the spine members 66 cause the inner bends 78 to sealingly contact the trocar T along the periphery or circumference thereof such that fluid cannot leak through the variable size passage while the trocar T is disposed therein. Seal 16 can be compressed a finite maximum amount by an instrument or object in variable size passage 69 without causing slit 32 in sleeve 18 to open. Accordingly, the variable size passage 69 can be enlarged to a maximum cross sectional size without sleeve 18 being moved to the expanded position. Therefore, instruments or objects having cross sectional sizes up to the maximum cross sectional size can be introduced in the variable size passage 69 in sealing relation with seal 16 while the sleeve 18 remains in the normal non-expanded position.

Depending on the size of the trocar, there will not be any gaps or spaces between the inner membrane section 68 and the trocar T such that the membrane 64 will sealingly engage trocar T entirely along the periphery or circumference thereof or there may be small gaps or spaces between the inner membrane section 68 and the trocar T along the periphery of the trocar. However, even where small gaps are present, leakage of fluid through the optical endoscopic portal 10 will still not occur due to the small cross sectional size of any gaps in relation to the length of the seal 16. It should be appreciated, therefore, that the variable size passage 69 does not have to be completely closed in the initial position for seal 16 since fluid will not leak through a slightly open variable size passage over the relatively greater length of the seal 16.

Figure 13:
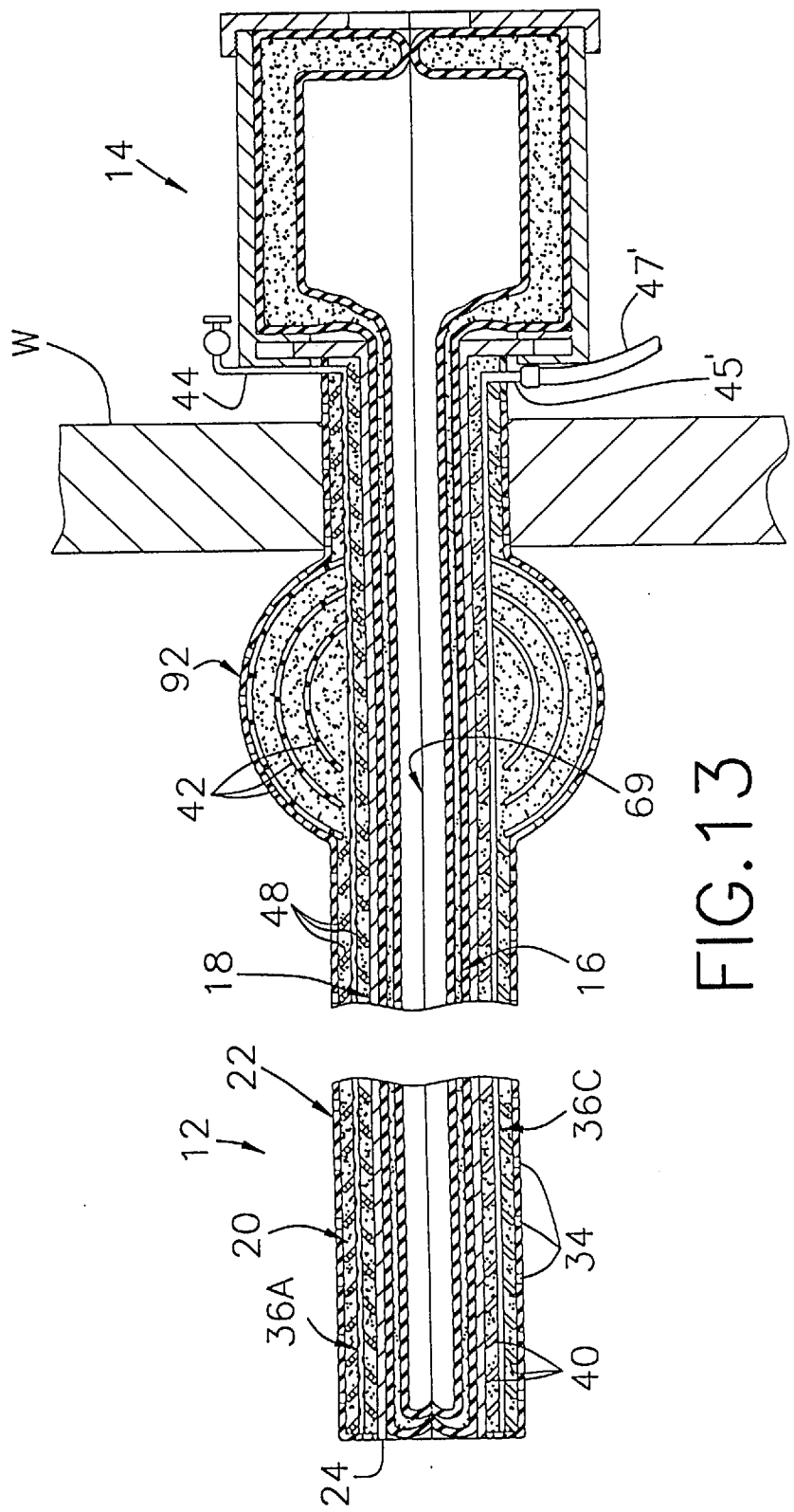
FIG. 13 is a broken, side sectional view of the optical endoscopic portal showing the cannula in the expanded configuration extending through a cavity wall with the liner in the closed position upon withdrawal of the trocar from the cannula.

When the trocar T is inserted through the optical endoscopic portal 10, a distal tip of the trocar T protrudes beyond the distal end of cannula 12 as shown in FIG. 11 for use in penetrating a body cavity wall. The distal tip of the trocar T is forced through the body cavity wall W creating a small size opening or puncture in the cavity wall, and the cannula 12 follows the trocar T through the cavity wall to position the sleeve distal end 24 within the body cavity as shown in FIG. 13. The opening or puncture formed in the cavity wall W and through which the cannula 12 extends corresponds in size to the external cross sectional size of the cannula in the non-expanded configuration with the absorbent member 20 in the dry state. The absorbent member 20 absorbs body fluids of the cavity wall W and within the body cavity, as permitted by holes 34 in membrane 22, as the cannula 12 passes through the cavity wall Wand enters the body cavity. Where there is insufficient body fluid to place the absorbent member 20 in the wet state, fluid can be supplied to the absorbent member 20 from externally of the body cavity via port 44 and spine member 36A, the fluid exiting the holes 48 in spine member 36A. Once in the wet state, the absorbent member 20 softens and expands diametrically or in a direction transverse or radial to the longitudinal axis of cannula 12, and the spine members 36 return to the normal extended configuration due to softening of the absorbent member 20. Accordingly, the cannula 12 will have an expanded configuration with an external diameter or cross section greater than the external diameter or cross section of the non-expanded configuration. With the absorbent member 20 in the wet state, straight branches 40 pivot outwardly and curved branches 42 spring outwardly from trunks 38 as shown in FIG. 13. Curved branches 42 form a rounded protuberance, bulge or bubble 92 at a predetermined location along cannula 12, the protuberance 92 being distally spaced from housing 14. Distally and proximally of protuberance 92, the cannula 12 has a uniform or substantially uniform external diameter, greater than the external diameter thereof in the non-expanded configuration. Accordingly, the external diameter or cross section of cannula 12 in the expanded configuration is non-uniform along the length thereof, distally of housing 14.

The protuberance 92 is disposed adjacent an internal surface of the cavity wall W with the cavity wall W being disposed between the protuberance 92 and the housing 14. Protuberance 92 prevents backing out of the cannula 12 from the body cavity and forms a stabilizer for the optical endoscopic portal 10 while housing 14 prevents the cannula from entering too far into the cavity. The portion of cannula 12 extending through the cavity wall W forms a seal along the length of the puncture or opening, i.e. along the thickness of the cavity wall W, due to diametric or transverse expansion of cannula 12, and the opening in the cavity wall W will stretch non-traumatically to accommodate the larger external diameter or cross sectional size of cannula 12. Fluids such as insufflation gas and/or medicaments can be introduced in the body cavity via port 44 and the spine member 36A where the spine member 36A is provided without holes 48, and fluids can be introduced in the body cavity through seal 16 upon withdrawal of trocar T therefrom and opening of variable size passage 69. Once the distal end of cannula 12 is positioned in the body cavity, the trocar T is withdrawn from the optical endoscopic portal 10, and the seal 16 automatically returns to the closed position due to the bias of spine members 66 and compressible member 62 on inner membrane section 68 as shown in FIG. 13.

With the distal end of the optical endoscopic portal 10 positioned in the body cavity, light is supplied to the body cavity by light transmitting spine member 36B which receives light from the light source via light guide 47. Accordingly, the body cavity is illuminated to facilitate observation or viewing, via the viewing device, of an operative procedure to be performed therein. The image transmitting spine member 36C receives and transmits an image of the body cavity to the viewing device via image guide 47', and the body cavity and operative procedure are visualized or viewed with the viewing device. Fluid can be introduced via the cannula 12, such as through the spine member 36A when the spine member 36A is provided without holes but has an open distal end, to clean or wipe the distal ends of the light and image transmitting spine members 36B and 36C, respectively.

Figure 14:
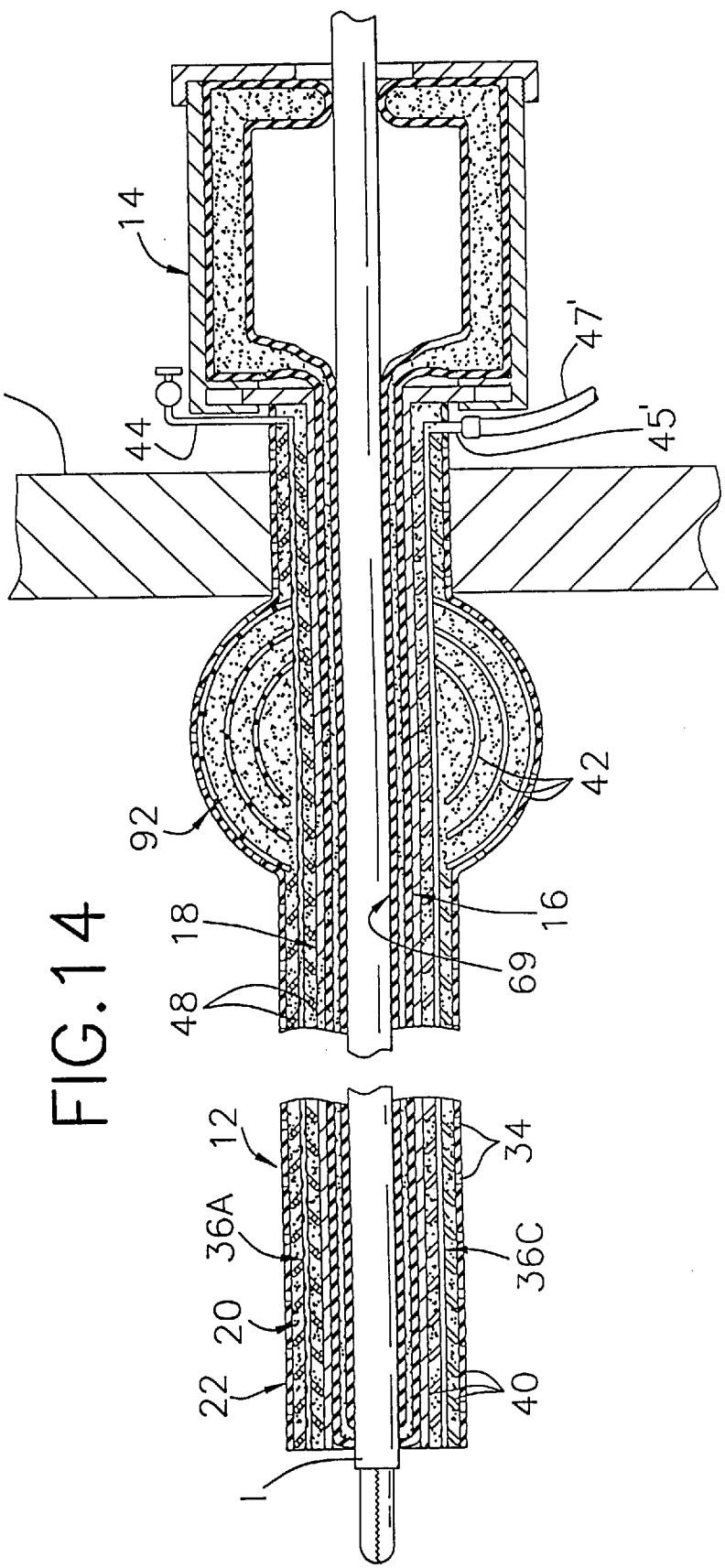
FIG. 14 is a broken side view, partly in section, of the optical endoscopic portal showing the cannula in the expanded configuration extending through the cavity wall with the liner in a further open position to receive an instrument through the cannula.

Various instruments of diverse sizes can be introduced in the body cavity and various size objects can be withdrawn from the body cavity through the optical endoscopic portal 10 in accordance with the operative procedure to be performed. FIG. 14 illustrates an instrument I, having a cross sectional size larger than the cross sectional size of trocar T, introduced through the optical endoscopic portal 10 to position a distal end of the instrument I in the body cavity while a proximal end of the instrument I remains external of the body cavity. As with trocar T, instrument I is introduced through the passage 69 of seal 16 causing the seal 16 to move from the normal closed position to the open position to enlarge the variable size passage 69 to accommodate the instrument I. The inner membrane section 68 sealingly contacts the instrument I entirely or substantially entirely along the periphery or circumference thereof to form a seal therewith while the sleeve 18 remains in the normal non-expanded position with slit 32 closed, since the cross sectional size of instrument I does not exceed the maximum cross sectional size to which variable size passage 69 can be enlarged without expanding the lumen of sleeve 18.

Instrument I is illustrative of a cutting instrument that can be utilized to excise anatomical tissue or structure, such as an organ, within the body cavity. The excised organ, for example the gall bladder, can be withdrawn from the body cavity through the optical endoscopic portal 10; and, when the size of the excised organ exceeds the maximum cross sectional size to which variable size passage 69 can be enlarged without expanding the lumen of sleeve 18, the sleeve 18 is moved to the expanded position to increase the size of the sleeve lumen to accommodate further diametric expansion of seal 16 and further enlargement of variable size passage 69 to receive the organ. The organ can be introduced in the variable size passage 69 directly to forcefully move sleeve 18 to the expanded position, or the organ can be withdrawn through a tubular expander introduced in the variable size passage 69 to further open seal 16 and expand sleeve 18.

FIG. 15, which does not show the branches 40 and 42 of trunks 38, illustrates a tubular expander E, having a lumen with a cross sectional size large enough to accommodate the excised organ O, introduced in variable size passage 69 as described above for introduction of trocar T and instrument I. Introduction of tubular expander E in variable size passage 69 causes spine members 66 to pivot or deflect such that trunks 84 are no longer oriented radially with respect to the longitudinal axis of seal 16. Compressible member 62 is compressed and pleats 72 are pivoted or deflected to accommodate the tubular expander E in the variable size passage 69. Accordingly, sleeve 18 is moved from the normal non-expanded position to the expanded position with slit 32 being opened to increase the diameter or cross sectional size of the sleeve lumen to accommodate the seal 16, which also expands diametrically. Seal 16 forms a seal with the tubular expander E, and the organ O is withdrawn from the body cavity through the lumen of the expander E. Various instruments can be introduced in and withdrawn from the body cavity through the tubular expander E. Since the sleeve 18 is moved to the expanded position by expander E, the cannula 12 will be mechanically expanded to a further expanded configuration wherein the external diameter or cross sectional size of the cannula 12 is greater than it is without diametric expansion of sleeve 18. The cavity wall will stretch non-traumatically to accommodate the increased external diameter or cross sectional size of the cannula. Accordingly, various instruments and other objects having cross sectional sizes greater than the maximum cross sectional size of the variable size passage 69 prior to expansion of sleeve 18 can be introduced in and/or withdrawn from the body cavity through seal 16, with or without the use of an expander, due to expansion of sleeve 18 when the variable size passage 69 is enlarged beyond the maximum cross sectional size.

The cannula 12 in the wet state can be used for various additional purposes or functions including contacting and/or manipulating tissue in the cavity to improve access, visibility or maneuverability, to treat tissue, to apply pressure to control bleeding, to absorb blood or other substances, to take tissue or culture samples, to deliver medicaments or therapeutic agents and to irrigate and/or evacuate. In order to withdraw the optical endoscopic portal 10 from the cavity wall W, the optical endoscopic portal 10 is moved proximally through the opening in the cavity wall W causing the cannula 12 to be forcefully withdrawn through the cavity wall W with the protuberance 92 collapsing or contracting to facilitate withdrawal. Prior to withdrawal from the cavity wall W, fluid can be evacuated from the absorbent member 20 via the spine member 36A when the port 44 is connected to a source of suction or vacuum. Evacuation of fluid from absorbent member 20 performs a "drying" function causing the absorbent member 20 to collapse, contract or compress such that the external size and/or configuration of cannula 12 is reduced to facilitate removal through the cavity wall.

Figure 16:
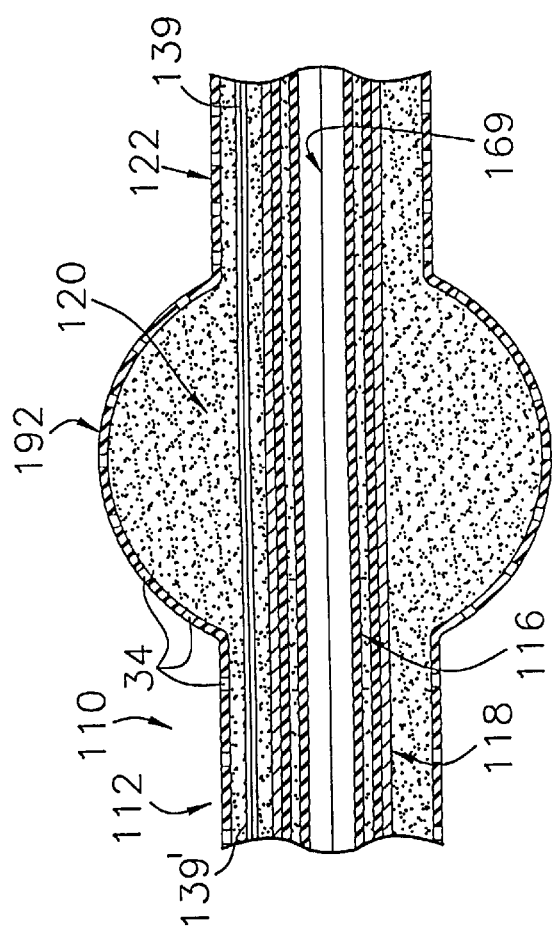
FIG. 16 is a broken, side sectional view of a modification of an optical endoscopic portal wherein the cannula does not have a spine.

FIG. 16 illustrates an alternative optical endoscopic portal 110 having a cannula 112 with light transmitting and image transmitting optical elements that do not function as a spine. Cannula 112, which is shown with absorbent member 120 in the wet state, is similar to cannula 12 except that a light transmitting optical element 139 and an image transmitting optical element 139' are embedded in absorbent member 120 without functioning or being shaped as a spine. In optical endoscopic portal 110, the shape of cannula 112 in the expanded configuration is determined by the absorbent member 120 without a spine. The absorbent member 120 expands diametrically a greater amount along a portion of the length of cannula 112 to form external, rounded protuberance 192 when the absorbent member 120 is in the wet state. The portion of absorbent member 120 corresponding to protuberance 192 has a cell or pore density substantially greater than the cell or pore density of the remainder of the absorbent member 120. When the absorbent member 120 is in the wet state, the portion of absorbent member 120 corresponding to protuberance 192 expands outwardly to a greater size due to the greater cell or pore density thereof while the remainder of the absorbent member 120 expands outwardly to a lesser size.

The light transmitting optical element 139 and the image transmitting optical element 139' do not have extended and contracted configurations since the light and image transmitting optical elements 139 and 139' do not shape the absorbent member 120 in the wet state. The light transmitting optical element 139 and the image transmitting optical element 139' are each a fiber optic cable coupled with light and image couplers (not shown), respectively, at a proximal end of the cannula 112. The fiber optic cables 139 and 139' are arranged in absorbent member 120 in side by side relation parallel with a longitudinal axis of the optical endoscopic portal 110; however, the fiber optic cables 139 and 139' can be arranged in absorbent member 120 in many various ways including non-parallel with the longitudinal axis of the optical endoscopic portal and not in side by side relation. The light and image transmitting optical elements 139 and 139' remain parallel with the optical endoscopic portal longitudinal axis when the cannula 112 is in the expanded configuration with the absorbent member 120 in the wet state. However, the optical elements 139 and 139' can be deformed by the absorbent member 120 in the wet state to follow the configuration of the absorbent member rather than the absorbent member being shaped by the optical elements as described for cannula 12.

Figure 17:
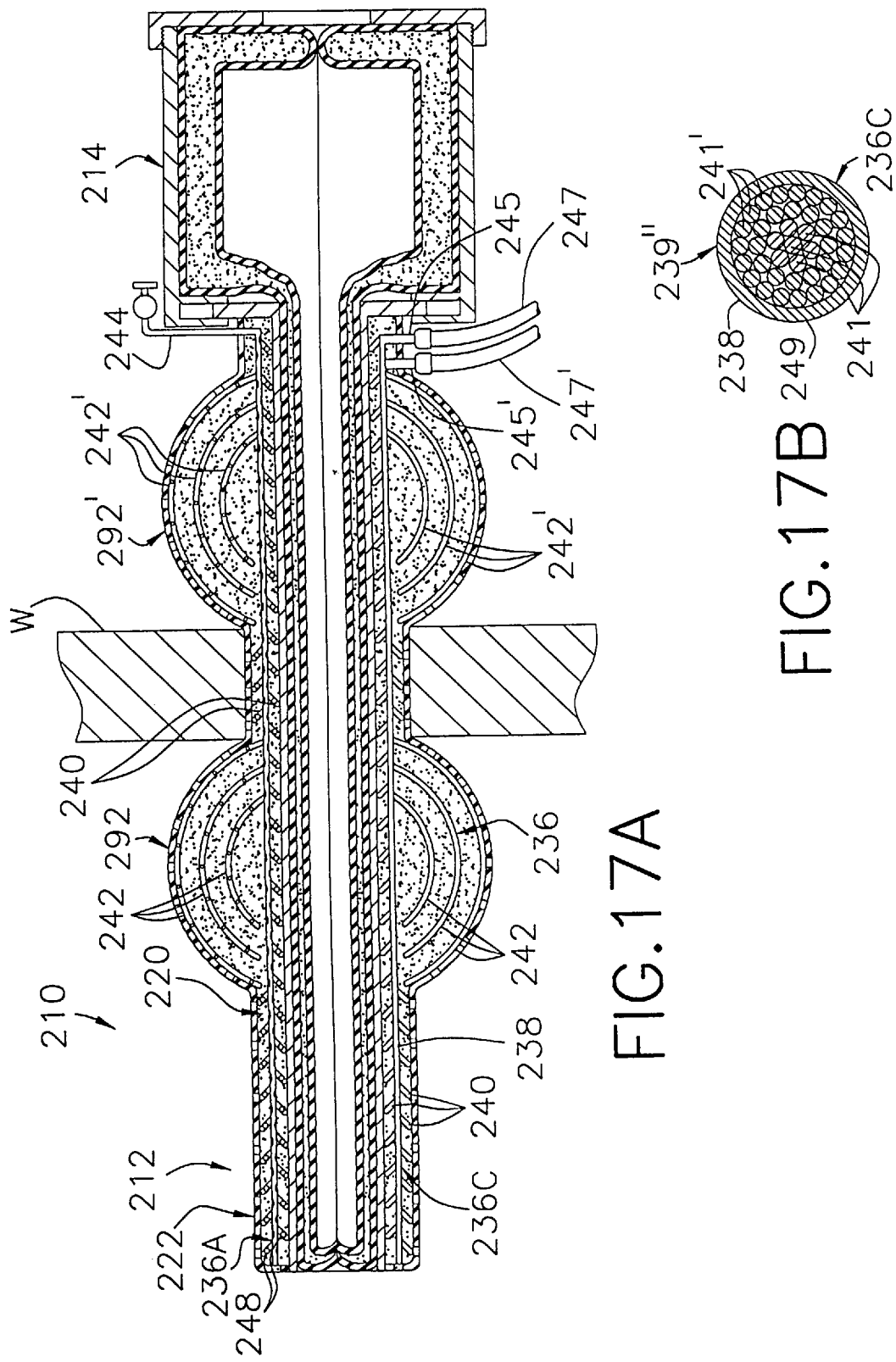
FIG. 17A is a broken, side sectional view of another modification of an optical endoscopic portal having a cannula forming a plurality of external protuberances in the expanded configuration.
FIG. 17B is a sectional view of a spine member for the cannula of the optical endoscopic portal of FIG. 17A.

FIG. 17A illustrates an optical endoscopic portal 210 provided with an external protuberance 292' longitudinally spaced from external protuberance 292 in the expanded configuration for cannula 212. Protuberance 292' is disposed just distally of housing 214 and protuberance 292 is distally spaced from protuberance 292' with the cavity wall W being held between the protuberances 292 and 292'. Spine members 236, which determine the shape of cannula 212 in the expanded configuration, are similar to spine members 36 except that spine members 236 include curved branches 242 defining protuberance 292 and curved branches 242' defining protuberance 292' with straight branches 240 between protuberances 292 and 292'. Protuberance 292 is disposed adjacent an internal surface of cavity wall W and prevents cannula 212 from backing out of the body cavity. Protuberance 292' is disposed adjacent an external surface of cavity wall W and prevents cannula 212 from moving farther than desired into the cavity. Since protuberance 292' is disposed externally of the body cavity, it is desirable that the absorbent member 220 be supplied with fluid actively such as via spine member 236A having holes 248 and communicating with fluid supply conduit or port 244 disposed externally of the body cavity. Spine member 236C of optical endoscopic portal 210 is both a light transmitting and image transmitting spine member with at least the trunk 238 thereof formed as a light and image transmitting optical element 239" including a plurality of light transmitting fibers 241 and a plurality of image transmitting fibers 241 ' in an outer sheath 249 as shown in FIG. 17B. The plurality of light transmitting fibers 241 are connected with a light coupler 245 disposed externally of the cavity wall W, and the plurality of image transmitting fibers 241' are connected with an image coupler 245' disposed adjacent the light coupler 245. The light coupler 245 and image coupler 245' are connected with light and image guides 247 and 247', respectively. The cannula 212 is particularly useful in cavity within a cavity procedures.

Figure 19:
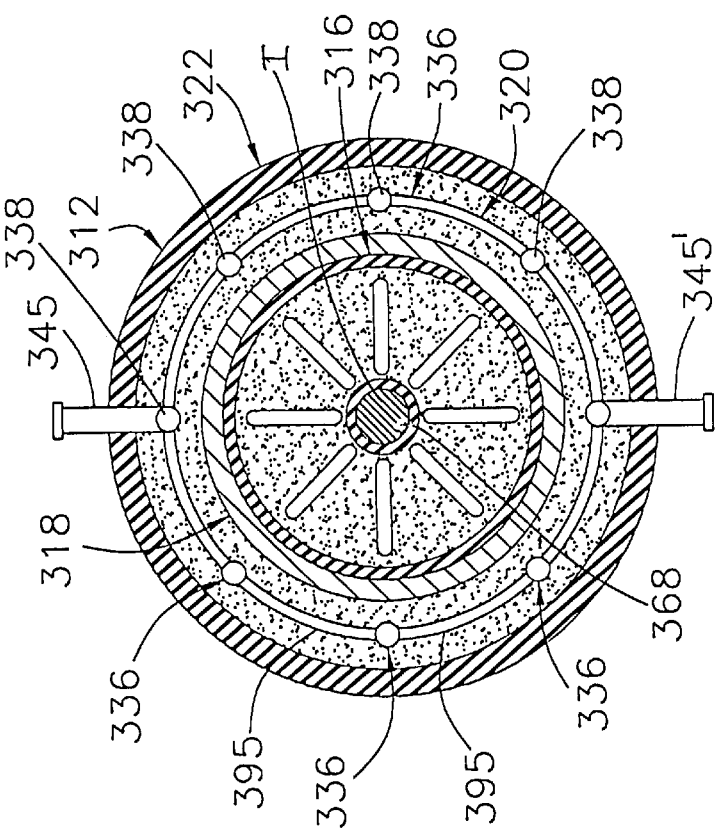
FIG. 19 is a sectional view of the optical endoscopic portal of FIG. 18 showing the cannula in the non-expanded configuration with the liner in an open position receiving an instrument therethrough in sealing relation.
Figure 18:
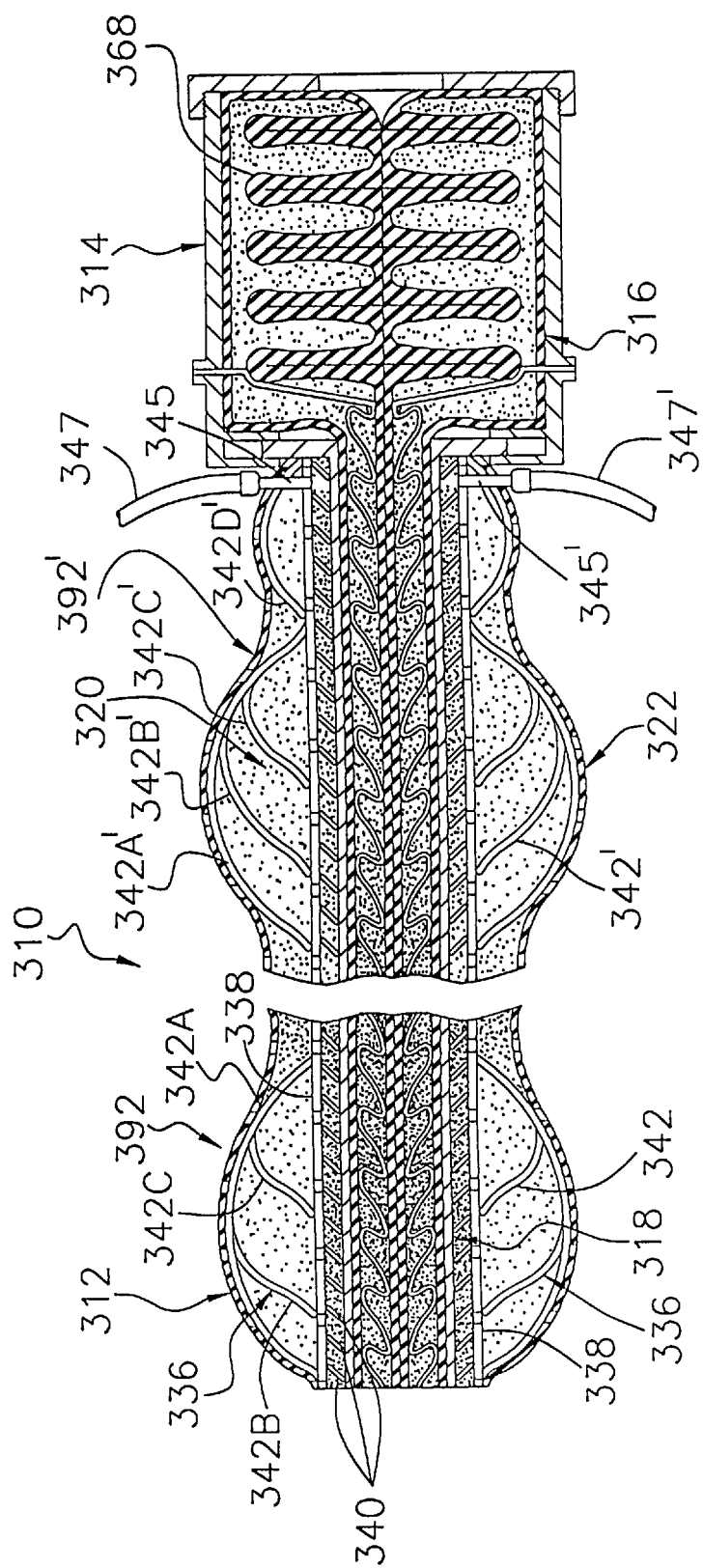
FIG. 18 is a broken, side sectional view of a further modification of an optical. endoscopic portal showing the cannula in the expanded configuration.

Another modification of an optical endoscopic portal is illustrated at 310 in FIG. 18 wherein the absorbent member 320 is shown in the wet state. Spine members 336 disposed in absorbent member 320 provide longitudinally spaced protuberances 392 and 392' along cannula 312 when the absorbent member 320 is in the wet state. Each spine member 336 includes a trunk 338 extending longitudinally through absorbent member 320 and straight branches 340 and curved branches 342 and 342' extending from trunk 338. The trunks 338 of the spine members 336 are arranged at 45° spaced locations about the longitudinal axis of cannula 312 as shown in FIG. 19, which does not show branches 340, 342 and 342'. Each spine member 336 has a normal extended configuration shown in FIG. 18 wherein straight branches 340 extend angularly, distally from the trunk 338 in the direction of sleeve 318, the branches 340 being longitudinally spaced from one another along the trunk 338 and being parallel with one another. Curved branches 342 define protuberance 392 and include, for each spine member 336, an outer curved branch 342A curving outwardly from the trunk 338, and inner curved branches 342B and 342C curving inwardly from the outer branch 342A in the direction of sleeve 318. Branch 342A has a first end pivotally, resiliently or flexibly attached to the associated trunk 338 and a second, free or unattached end adjacent the associated trunk 338. Branches 342B and 342C have first ends pivotably, resiliently or flexibly attached to the associated branch 342A and second, free or unattached ends adjacent the associated trunk 338. Curved branches 342 define protuberance 392', which is proximally spaced from protuberance 392, and include, for each spine member 336, an outer curved branch 342A', inner curved branches 342B' and 342C' and a curved branch 342D' disposed proximally of outer branch 342A'. Branches 342A', 342B' and 342C' are similar to branches 342A, 342B and 342C. Branch 342D', which curves outwardly from the corresponding trunk 338, has a first end pivotably, flexibly or resiliently mounted to the corresponding trunk 338 and a second, free or unattached end adjacent the corresponding trunk 338 with the second end of branch 342D' being disposed just proximally of or adjacent the first end of corresponding branch 342A'. For each spine member 336, the branches 340, 342 and 342' are disposed in the same plane as the associated trunk 338 and such plane contains the cannula longitudinal axis. The branches 340 are pivoted toward the associated trunks 338 and the branches 342 and 342' are compressed or flattened toward the associated trunks 338 to be disposed close to or in substantial alignment with the associated trunks 338 in the contracted configuration when the absorbent member 320 is in the dry state. In the wet state for absorbent member 320, the spine members 336 return to the normal extended configuration with branches 342A, 342B and 342C of the spine members defining round external protuberance 392 and branches 342A', 342B', 342C' and 342D' of the spine members defining pear-shaped external protuberance 392' for cannula 312 in the expanded configuration. During use, one or both of the protuberances 392 and 392' can be introduced in the body cavity and the protuberances can be utilized to manipulate tissue or organ structure within a body cavity, and/or to stabilize the optical endoscopic portal 310 relative to the body cavity wall.

One or more of the spine members 336 can be a light transmitting and/or image transmitting spine member. In the case of optical endoscopic portal 310, each of the spine members 336 is both a light transmitting and image transmitting spine member constructed in a manner similar to the light and image transmitting spine member 236C. The light transmitting fibers of spine members 336 are coupled with a light coupler 345, and the image transmitting fibers of spine members 336 are coupled with an image coupler 345'. Accordingly, the light and image transmitting spine members 336 have arcuate or circumferential segments 395 extending circumferentially through absorbent member 320 at the proximal end thereof and to meet or joint couplers 345 and 345', respectively, as shown in FIG. 19. The couplers 345 and 345' are in turn coupled with light guide 347 and image guide 347', respectively as shown in FIG. 18.

Seal or liner 316 for optical endoscopic portal 310 is different from seal 316 in that the inner membrane section 368 is not pleated along the cannula portion and is pleated differently than seal 316 along the housing portion, the seal 316 being described in application Ser. No. 08/651,284 filed May 22, 1996, the disclosure of which is incorporated herein by reference. The seal 316 is shown in FIG. 19 in an open position receiving an instrument I therethrough in sealing relation.

FIGS. 20–22 illustrate various modifications of light transmitting and/or image transmitting spine members for controlling the external configurations of the cannulas of the optical endoscopic portals in the cannula expanded configuration when the absorbent members are in the wet state. FIG. 20 illustrates a light transmitting spine member 436 having a straight trunk 438 and curved branches 442 curving outwardly from trunk 438 in the normal extended configuration. Alternate branches 442 protrude from opposite sides of trunk 438, and each curved branch 442 is provided with a plurality of straight branches 440 extending outwardly from curved branches 442 in a direction away from trunk 438 in the extended configuration. Straight branches 440 are pivotally, resiliently or flexibly attached to curved branches 442. The curved branches 442 are compressed or flattened toward trunk 438 and the straight branches are pivoted toward the curved branches in the contracted configuration. Trunk 438 is formed of an outer sheath 449 surrounding a plurality of light transmitting fibers 441.

FIG. 21 illustrates an image transmitting spine member 536 having a straight trunk 538 and curved branches 542 protruding from trunk 538 in the extended configuration. Branches 542 are disposed in parallel planes, respectively, in the extended configuration and are spaced longitudinally from one another along trunk 538. Each branch 542 has first and second ends attached to trunk 538, and the branches 542 are pivotable toward trunk 538 to lie close to trunk 538 in the contracted configuration. Branches 542 can be of different sizes such as a large middle branch or loop arranged between two smaller branches or loops. The trunk 538 is formed of an outer sheath 549 surrounding a plurality of image transmitting fibers 541'.

The spine member 636 illustrated in FIG. 22 is a light and image transmitting spine member comprising a straight trunk 638 and a curved branch 638 protruding outwardly from trunk 638 in the extended configuration. Branch 642 is disposed in the same plane as trunk 638 and has a first end pivotably, flexibly or resiliently attached to trunk 638 and a free or unattached second end adjacent trunk 638. A plurality of Y-shaped branches 640 extend outwardly from branch 642 in a direction away from trunk 638 in the extended configuration, and each Y-shaped branch 640 has an end or base pivotally, resiliently or flexibly attached to curved branch 642. Curved branch 642 is compressed or flattened toward trunk 638, and branches 640 are pivoted toward curved branch 642 in the collapsed or contracted configuration. The trunk 638 is formed of an outer sheath 649 surrounding a plurality of light transmitting fibers 641 and a plurality of image transmitting fibers 641'.

Figure 23:
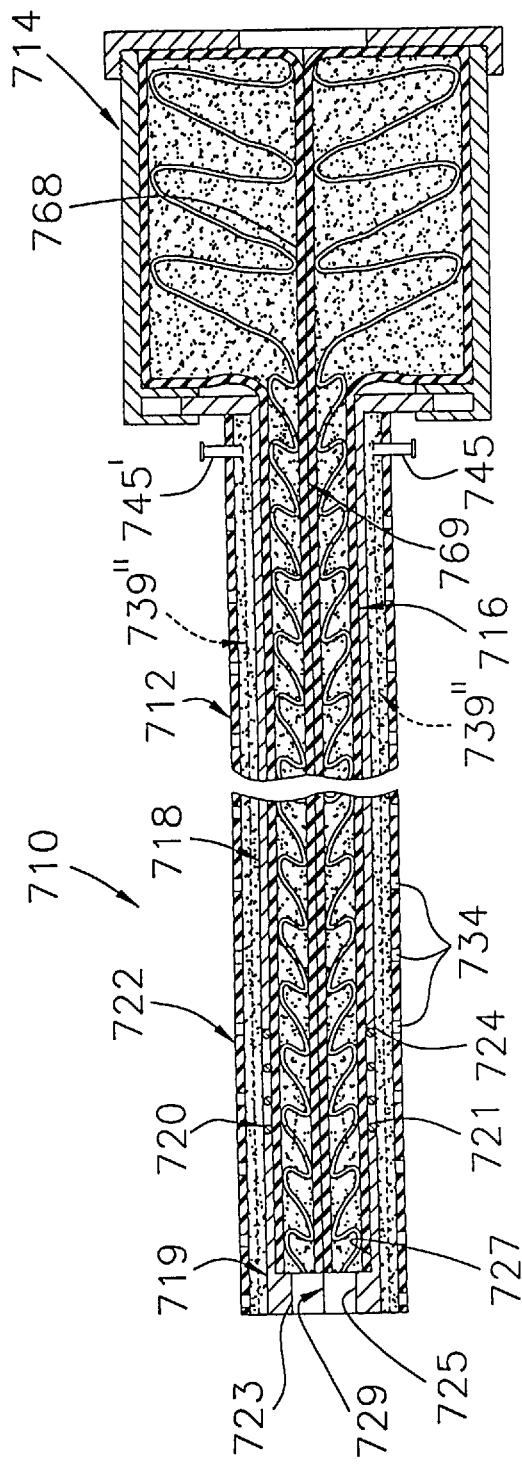
FIG. 23 is a broken, side sectional view of a further modification of an optical endoscopic portal showing the absorbent member in the dry state with a safety shield of the cannula in a retracted position.

A further modification of an optical endoscopic portal is illustrated at 710 in FIG. 23, optical endoscopic portal 710 being representative of an optical endoscopic portal wherein the cannula includes a spring biased safety shield. The distal end 724 of sleeve 718 of cannula 712 of optical endoscopic portal 710 terminates proximally of the distal ends of absorbent member 720 and membrane 722, respectively, which are aligned with one another. A safety shield 719 is concentrically disposed in absorbent member 720 distally of sleeve 718, and a helical coil spring 721, disposed concentrically around seal 716, is interposed between sleeve 718 and shield 719. Shield 719 is tubular or hollow and has an external diameter the same as the external diameter of sleeve 718, a blunt distal end 723 and an inwardly protruding annular shoulder 725 at the distal end 723. The distance that shoulder 725 protrudes inwardly from an internal surface 727 of shield 719 corresponds to the thickness of seal 716 when the seal 716 is compressed the finite maximum amount by an instrument introduced therethrough such that the shoulder 725 will engage the instrument. Spring 721 is connected to sleeve 718 and to shield 719 and biases shield 719 distally relative to sleeve 718 to an extended position wherein shield distal end 723 is spaced a maximum or first distance distally from the distal end 724 of sleeve 718. However, when the absorbent member 720 is in the dry state prior to use, the shield 719 is maintained, constrained or held in a retracted position, shown in FIG. 23, wherein the shield distal end 723 is spaced a minimum or first distance from the sleeve distal end 724, the first distance being greater than the second distance. As shown in FIG. 23, the shield distal end 723 in the retracted position is aligned with the distal ends of absorbent member 720 and membrane 722, respectively.

Shield 719 is maintained, held or constrained in the retracted position by absorbent member 720 in the dry state such that the stiffness and rigidity of the absorbent member in the dry state prevents movement of the shield 719 to the extended position. When the absorbent member 720 is in the wet state, the constraining force of the absorbent member 720 on shield 719 is released or lessened due to the resulting flexibility and softness of the absorbent member, and the spring 721 moves the shield 719 distally relative to the sleeve 718 to the extended position wherein the shield distal end 723 is disposed further distally of the distal end 724 of sleeve 718. Seal 716, which is disclosed in application Ser. No. 08/651,284 filed May 22, 1996 and incorporated herein by reference, is disposed within sleeve 718, housing 714 and shield 719 with a distal end of seal 716 disposed in abutment with shoulder 725 when the shield is in the retracted position.

Optical elements 739" are embedded in the thickness of absorbent member 720 and extend longitudinally therein. Each optical element 739" is a light and image transmitting optical element having light transmitting fibers and image transmitting fibers coupled to light coupler 745 and to image coupler 745', respectively. The optical elements 739" optically couple the distal end of cannula 712 with the proximal end thereof for illuminating a body cavity via the light transmitting fibers and for transmitting an image of a body cavity via the image transmitting fibers for viewing externally of the body cavity.

In order to use optical endoscopic portal 710 to establish a passage through a cavity wall, a trocar is introduced through the variable size passage 769 of seal 716 as described above for optical endoscopic portal 10. The distal tip of the trocar will protrude distally of the distal end 723 of shield 719 with the shield 719 in the retracted position. During penetration of a cavity wall with the trocar, the cannula 712 passes through the cavity wall with the trocar. As the cannula 712 passes through the cavity wall, the absorbent member 720 absorbs body fluids as permitted by holes 734 in membrane 722. Once the distal end of cannula 712 and, therefore, the distal ends of the absorbent member 720 and membrane 722, have passed through the cavity wall and entered the body cavity, the absorbent member 720 will be in the wet state and the shield 719 will be released for movement distally to the extended position by spring 721. In the extended position for shield 719, the distal end 723 of shield 719 is disposed distally of the distal tip of the trocar. Accordingly, the distal tip of the trocar is disposed in the shield 719 and is protected.

Upon removal of the trocar from the optical endoscopic portal 710, the seal 716 automatically returns to the closed position such that the variable size passage 769 therethrough is closed to prevent leakage of fluids. The shield 719 can have a slit 729 in the wall thereof extending the entire length of the shield to permit the lumen of shield 719 to be expanded along with sleeve 718 where the sleeve 718 is slit as previously described, when the absorb ember is in the wet state. It should be appreciated that where the absorbent member 720 is supplied with fluid passively via absorption of body fluids, the rate of absorption can be selected such that shield 719 is released for movement to the extended position as soon as the distal tip of the trocar has entered the body cavity. The optical elements 739" provide illumination and visualization of the body cavity from externally thereof. Operation and use of a safety shielded endoscopic portal is disclosed in greater detail in the prior application Ser. No. 08/651,284 filed May 22, 1996, the disclosure of which is incorporated herein by reference.

An additional modification of an optical endoscopic portal according to the present invention is illustrated at 810 in FIG. 24. Cannula 812 for optical endoscopic portal 810 includes absorbent member 820, a transparent stretchable membrane 822 concentrically disposed around absorbent member 820, a light and image transmitting spine member 836 disposed in absorbent member 820 and a seal 816, shown in FIG. 26, disposed in spine member 836. Spine member 836 is shown in FIG. 25 and comprises a trunk 838 configured as an elongate helical coil having a distal segment 831 and a proximal segment 833 made up of coils of the same uniform diameter or size and an intermediate segment 835 disposed between the distal and proximal segments and made up of coils of larger diameter or size. The number and size of the coils of the distal, proximal and intermediate segments can vary in accordance with the external configuration desired for cannula 812 in the expanded configuration when absorbent member 820 is in the wet state, the intermediate segment 835 having a large diameter coil interposed between two smaller diameter coils which in turn are connected to the still smaller diameter coils of the distal and proximal segments 831 and 833, respectively. The spine member 836 is the passage defining member for cannula 812, and the coils of trunk 838 are axially aligned to define a longitudinal passage or lumen, the trunk 838 terminating distally at a distal end 824 for being positioned in a body cavity and proximally at a proximal end for being disposed externally of the body cavity. The distal end 824 of trunk 838 is aligned or substantially aligned with the distal ends of absorbent member 820 and membrane 822 to define a distal end of cannula 812. A plurality of J-shaped branches 843 are attached to trunk 838 and have straight first ends pivotably, flexibly or resiliently attached to the coils of trunk 838 and second, free or unattached curved ends. The spine member 836 has a normal extended configuration wherein the coils of trunk 838 are spaced longitudinally from one another to define a uniform cylindrical configuration or diameter along the distal and proximal segments 831 and 833, respectively, and a rounded, protuberance 892 along the intermediate segment 835 with the branches 843 extending outwardly from trunk 838 as shown in FIG. 25. The spine member 836 is maintained in a contracted configuration shown in FIG. 24 by the absorbent member 820 in the dry state. In the contracted configuration, the trunk 838 is more tightly wound such that the coils thereof are in contact with one another with no spaces therebetween, and the coils of the intermediate segment 835 have the same diameter as the coils of the distal and proximal segments 831 and 833. In the contracted configuration, the branches 843 are pivoted or flattened toward the coils to be in substantial alignment therewith. A transverse flange 828 is provided at the proximal end of the cannula 812 and has an opening therein communicating with the lumen defined by trunk 838, the flange 828 being connected to trunk 838. If desired, the optical endoscopic portal 810 can be provided with a housing 814 as shown in dotted lines in FIG. 24, and the housing 814 can contain all or part of seal 816. Since the coils of trunk 838 are held adjacent or in contact with one another when the absorbent member 820 is in the dry state, the trunk 838 has a length when the absorbent member is in the dry state that is less than the length of the trunk 838 when the absorbent member is in the wet state. Seal 816 is similar to seal 16 except that seal 816 does not have a housing portion, the seal 816 being concentrically disposed within the lumen or passage defined by the coils of trunk 838. The seal 816 is disposed in a normal closed position wherein the variable size passage 869 therethrough is closed as shown in FIG. 26 to prevent leakage through the optical endoscopic portal 810.

The spine member 836 is a light and image transmitting spine member and is also the passage defining member. At least the trunk 838 of spine member 836 is formed of an outer sheath 849 surrounding a plurality of light transmitting fibers 841 and a plurality of image transmitting fibers 841' as shown in FIG. 25. The light transmitting fibers 841 and the image transmitting fibers 841' are coupled with light coupler 845 and image coupler 845', respectively, extending in a radial direction from flange 828.

Prior to use, absorbent member 820 is in the dry state constraining or maintaining the spine member 836 in the contracted configuration. When it is desired to utilize optical endoscopic portal 810 to provide a passage through a body cavity wall, cannula 812 is passed through a cavity wall W, such as with a penetrating member or trocar introduced through variable size passage 869, to position the distal end 824 thereof within the body cavity and to position flange 828 in abutment with an external surface of the cavity wall W as shown in FIG. 27. If desired, the flange 828 can be provided with an adhesive or tissue gripping elements or anchors for securing the flange 828 to the external surface of the cavity wall W. The absorbent member 820 absorbs body fluids as permitted by holes 834 in membrane 822 and expands radially or diametrically as well as longitudinally. Once the absorbent member 820 is in the wet state, spine member 836 returns to its normal extended configuration as shown in FIG. 27. The coils of trunk 838 unwind causing protuberance 892 to be formed adjacent an internal surface of the cavity wall W and causing the trunk 838 to lengthen or elongate. The cannula 812 will lengthen in the longitudinal direction such that the cannula itself performs a shielding function to protect the distal tip of a trocar introduced therethrough. Accordingly, the distal tip of the trocar will protrude beyond the distal end of the cannula 812 for penetration through the cavity wall W, at which time the cannula 812 is in a retracted position; and, upon entry in the body cavity, the distal tip of the trocar will be disposed within the cannula 812, at which time the cannula is in an extended position. With the cannula 812 in the extended position, the distal tip of the trocar will thusly be shielded or protected within the cannula. Light coupler 845 is connectible to a light source for illumination of the body cavity via spine member 836, and image coupler 845' is connectible to a viewing device for visualizing the body cavity, from externally of wall W, via the spine member 836.

FIG. 28 illustrates a spine member 936, similar to spine member 836, except that the spine member 936 is made up of an inner trunk 938A and an outer trunk 938B disposed concentrically around inner trunk 938. Spine member 936, the trunks 938A and 938B of which do not have branches, has a normal extended configuration wherein the coils of inner trunk 938A are longitudinally spaced from one another and are of uniform diameter and wherein the coils of outer trunk 938B are longitudinally spaced from one another and have a diameter greater than the uniform diameter of the inner trunk coils. The coils of the outer trunk 938B can be of a uniform diameter or a non-uniform diameter as shown in FIG. 28 wherein the outer trunk 938B has a large diameter coil interposed between two smaller diameter coils. The inner trunk 938A fits within the outer trunk 938B and both the inner and outer trunks are more tightly wound or coiled in the contracted configuration. The coils of the outer trunk 938B can be disposed between the coils of the inner trunk 938A in the contracted configuration. The inner and outer trunks 938A and 838B are maintained in the contracted configuration by an absorbent member in the dry state and return to the normal extended configuration when the absorbent member is in the wet state. The inner trunk 938A will unwind or uncoil and thusly expand in the longitudinal direction to increase the length of the cannula formed thereby, and the outer trunk 938B will unwind to form a protuberance 992 along the cannula when the absorbent members is in the wet state. The inner trunk 938A is formed of sheath 949 surrounding light transmitting fibers 941. The outer trunk 938B is formed of sheath 949' surrounding image transmitting fibers 941'. The fibers 941 and 941' are proximally connected to light and image couplers, respectively, disposed at a proximal end of the cannula.

Figure 29:
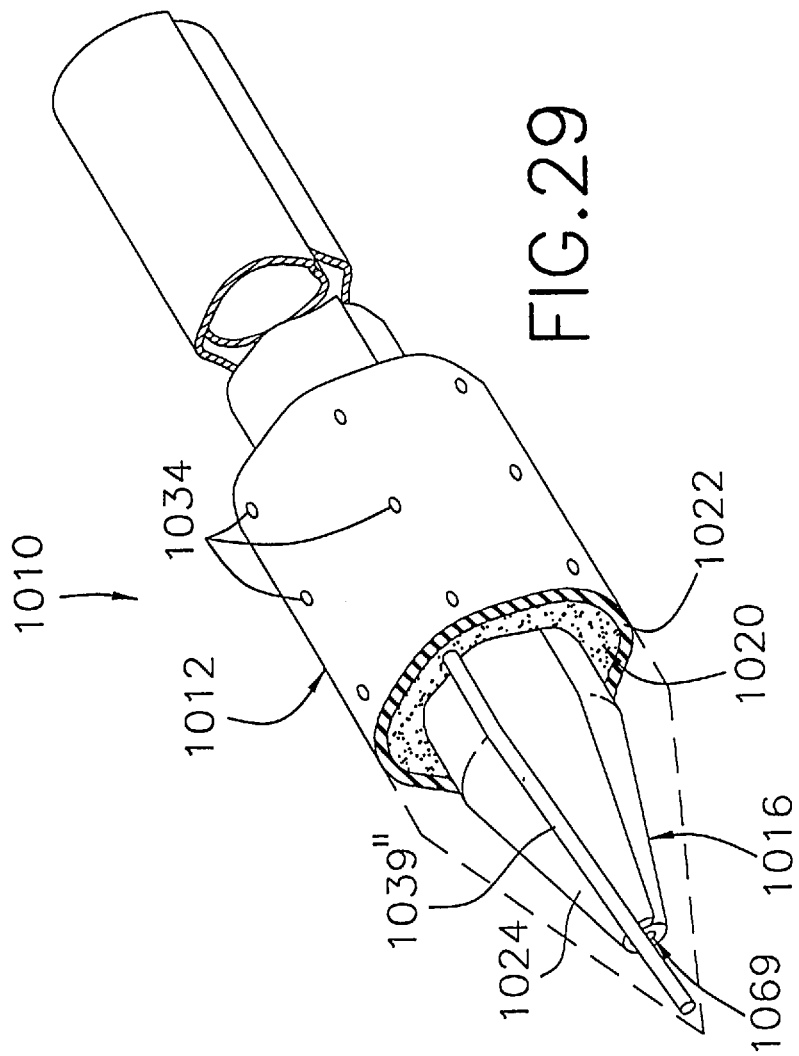
FIG. 29 is a broken perspective view of an additional modification of an optical endoscopic portal showing the absorbent member in the dry state.

Another modification of an optical endoscopic portal is illustrated at 1010 in FIG. 29, only a distal portion of the optical endoscopic portal 1010 being shown. Cannula 1012 for optical endoscopic portal 1010 comprises a liner 1016, an absorbent member 1020 disposed over liner 1016 and a stretchable membrane 1022 disposed over the absorbent member 1020. The liner 1016 is in the nature of an elongate rolled member and includes a thin sheet or layer of non-breakable, biologically compatible or inert material rolled about a longitudinal axis to form a spiral. The rolled member 1016 has a conical or tapered distal end 1024 configured to penetrate a body cavity wall and a variable size passage 1069 extending longitudinally therethrough. The liner 1016 has a normal closed or initial position where the variable size passage 1069 is closed or substantially closed at distal end 1024. The liner 1016 is made of a resilient or spring material, such as plastic, to maintain the closed position therefor. However, since liner 1016 is maintained or constrained in the closed position by the absorbent member 1020 in the dry state, the liner 1016 does not have to be made of spring materials but can be made of non-spring materials such as paper, leather and silk. Since the liner 1016 is constrained by the absorbent member 1020 in the dry state, the variable size passage 1069 cannot be enlarged to receive an instrument when the absorbent member 1020 is in the dry state. The absorbent member 1020 surrounds the liner 1016, and a distal end of the absorbent member 1020 is tapered or pointed as shown in dotted lines in FIG. 29 for penetration through a body cavity wall, the membrane 1022 following the configuration of the absorbent member. The cannula 1012 is self-penetrating due to the tapered or pointed configuration of distal end 1024. However, the absorbent member 1020 does not have to come to a sharp point, in which case the cannula 1012 can still be utilized to penetrate a cavity wall with the assistance of a small skin incision as permitted by the tapered configuration of the cannula distal end.

A light and image transmitting optical element 1039" is disposed in absorbent member 1020 and contains light transmitting and image transmitting fibers (not shown). The light and image transmitting optical element 1039" follows the configuration of absorbent member 1020; and, therefore, the light and image transmitting optical element 1039" is bent or angled inwardly at a distal end thereof to follow the tapered or pointed configuration of the distal end of absorbent member 1020. The light and image transmitting optical element 1039" terminates distally at the distal end of the absorbent member 1020 and terminates proximally at light and image couplers (not shown) disposed externally of the cavity wall to be penetrated. Upon penetration into a body cavity with the cannula 1012, the light and image transmitting optical element 1039" provides illumination to the body cavity and visualization of the body cavity from externally of the cavity wall.

When the absorbent member 1020 is in the wet state, such as via absorption of body fluid through holes 1034, the liner 1016 can unroll or unwind to enlarge variable size passage 1069 to receive an instrument, and the absorbent member 1020 in the wet state causes the liner 1016 to sealingly engage the instrument. The light and image transmitting optical element 1039" can unbend, deflect or deform as the liner 1016 unrolls or unwinds to receive an instrument. The liner 1016 returns to its normal closed position after withdrawal of the instrument therefrom due to the resilience or force of the liner itself and/or due to the compressive force of absorbent member 1020 or an externally applied resilience or force, and the light and image transmitting optical element 1039" will move with the liner and the absorbent member. Where the variable size passage is not sufficiently small in the normal closed position to prevent leakage of fluid therethrough, a valve, such as a flapper or trumpet valve, can be utilized in the optical endoscopic portal 1010.

Figure 31:
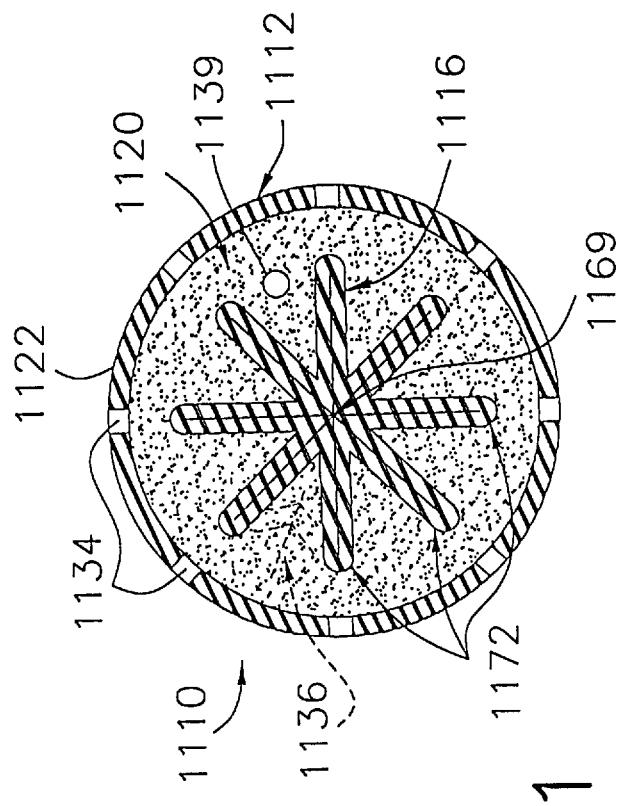
FIG. 31 is a sectional view of the cannula of FIG. 30.
Figure 30:
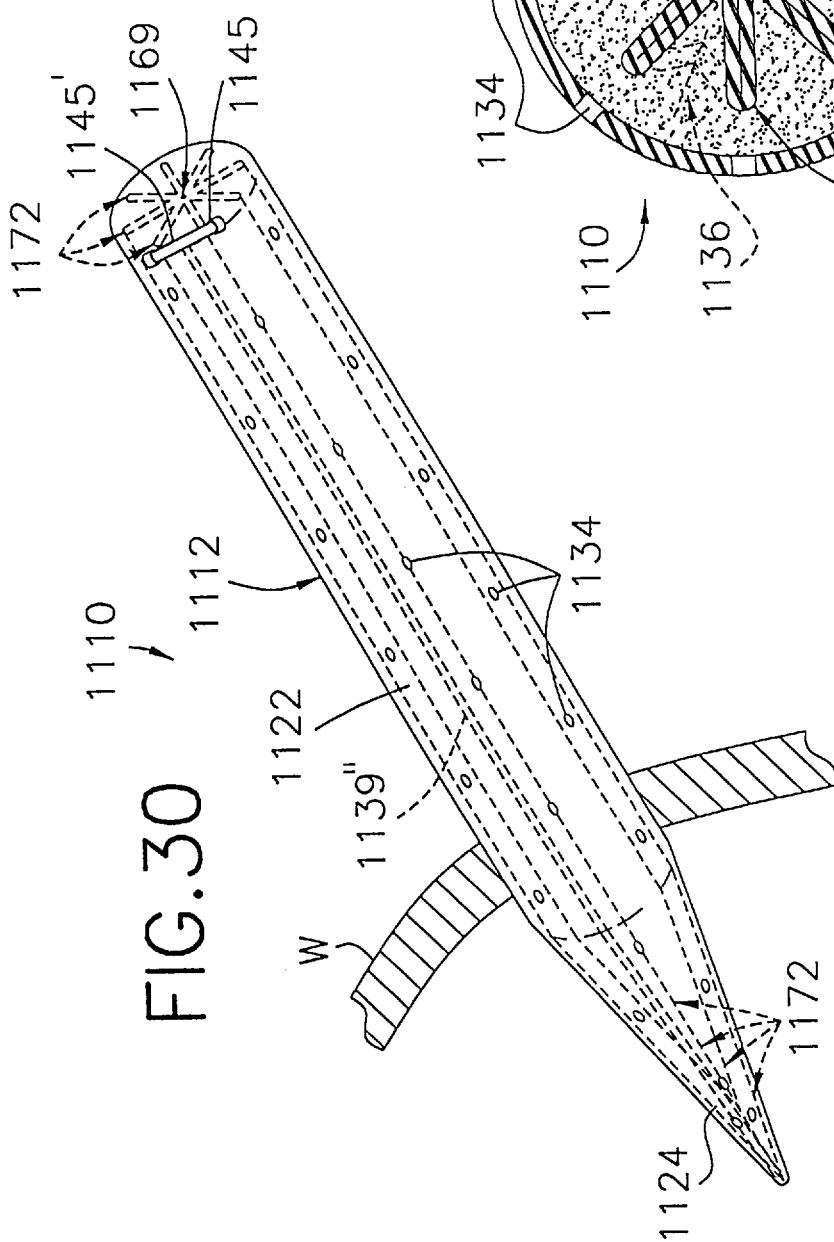
FIG. 30 is a perspective view of an additional modification of an optical endoscopic portal showing the cannula extending through a body cavity wall.

Another modification of an optical endoscopic portal according to the present invention is illustrated at 1110 in FIGS. 30 and 31. Cannula 1112 for optical endoscopic portal 1110 comprises an absorbent member 1120, a liner 1116 disposed in the absorbent member 1120 and a transparent stretchable membrane 1122 disposed around absorbent member 1120. Cannula 1112 is similar to seal 16 without the housing portion, since optical endoscopic portal 1110 does not have a housing.

Liner 1116 is similar to the inner membrane section 68 of seal 16 and includes radial pleats 1172 disposed about variable size passage 1169. Membrane 1122 is connected to liner 1116 at the distal and proximal ends of the absorbent member 1120 and is similar to the outer membrane section 70 of seal 16 except that membrane 1122 has holes 1134. The membrane 1122 and the liner 1116 form an envelope or bag enclosing absorbent member 1120 with the material of the absorbent member being disposed between liner 1116 and membrane 1122 and between adjacent pleats 1172. A distal end of absorbent member 1120 has a configuration to penetrate an anatomical cavity wall and defines a distal end 1124 of cannula 1112, the distal end 1124 being tapered or conical to terminate distally at a tip for penetrating anatomical tissue. The membrane 1122 fits snugly over the dry absorbent member 1120, and the pleats 1172 of liner 1116 extend through the distal end 1124 as shown in dotted lines in FIG. 30. Accordingly, the pleats 1172 are of decreasing or diminishing radial size or length along distal end 1124. It should be appreciated that the liner 1116 can be scrunched into a lumen or recess of absorbent member 1120 to form random pleats or folds as disclosed in application Ser. No. 08/651,284 incorporated herein by reference.

A light and image transmitting optical element 1139" is disposed in absorbent member 1120 and has a distal end terminating at or adjacent the distal end of the absorbent member 1120. The light and image transmitting element 1139" includes light transmitting fibers (not shown) coupled to light coupler 1145 and image transmitting fibers (not shown) coupled to image coupler 1145', the light and image couplers being disposed at the proximal end of cannula 1112. The light and image transmitting optical element 1139" provides illumination of a body cavity and transmits an image of the body cavity for external viewing when the couplers 1145 and 1145' are coupled to a light source and a viewing device, respectively.

Prior to introduction in a body cavity, absorbent member 1120 is in the dry state such that the cannula 1112 is rigid and pencil-like. The liner 1116 is disposed in the initial position wherein variable size passage 1169 is closed as shown in FIG. 31. The variable size passage 1169 cannot be opened or enlarged as long as the absorbent member 1120 is in the dry state. With the absorbent member 1120 in the dry state, the cannula 1112 is used to penetrate a body cavity wall W to position the distal end 1124 within the body cavity while the proximal end of the cannula remains external of the body cavity. During passage through the cavity wall W and upon entry of the distal end 1124 in the body cavity, the absorbent member 1120 absorbs body fluids via holes 1134. The absorbent member 1120 will then be in the wet state; and, depending on the type of material forming the absorbent member 1120, the cannula 1112 can expand diametrically in the wet state, with or without formation of an external protuberance, to form a seal along the thickness of the cavity wall W. The distal end 1124 of the cannula will become soft and blunt to protect tissue and organ structure within the cavity. The body cavity is illuminated and an image of the body cavity is provided externally of wall W via the light and image transmitting optical element 1139" as permitted due to the transparency of membrane 1122. It should be appreciated, however, that the light and image transmitting optical element can protrude through the membrane 1122 at the distal end of the cannula; and, therefore, the membrane 1122 does not have to be transparent. The cannula 1112 can be manipulated or moved, from externally of wall W, to position the distal end thereof to optimize viewing. The wet absorbent member 1120 maintains the liner 1116 in the closed or initial position while permitting the variable size passage 1169 to be enlarged to receive an instrument. The absorbent member 1120 biases the liner 1116 into sealing engagement with the introduced instrument; and, when the instrument is withdrawn from the cannula, the absorbent member 1120 biases the liner to return to the initial position. If desired, one or more spine members, such as spine member 1136 shown in dotted lines in FIG. 31, can be provided in the absorbent member 1120 to bias the liner 1116 to the initial position and/or to control the external configuration of cannula 1112 in the expanded configuration, the spine member 1136 being similar to spine member 66. Where a spine member is provided in absorbent member 1120, the light and image transmitting optical element can form the spine member. Visualization and illumination can be facilitated by forming the absorbent member 1120 of optically clear material.

Another modification of an optical endoscopic portal is illustrated in FIGS. 32 and 33 at 1210, the cannula 1212 for optical endoscopic portal 1210 being formed of an absorbent member 1220. Cannula 1212 includes an elongate absorbent member 1220 having a conical or tapered distal end 1224 for penetrating an anatomical cavity wall and terminating proximally at a transverse flange 1228. A light and image transmitting optical element 1239", similar to light and image transmitting element 1139", is disposed in the absorbent member 1220 and terminates distally at or adjacent the distal end 1224. The light and image transmitting optical element 1239" is bent or angled to follow the taper of distal end 1224 in the dry state, and the distal end of the light and image transmitting optical element 1239" is flush with the absorbent member 1220. A proximal end of light and image transmitting optical element 1239" is coupled to light coupler 1245 and image coupler 1245', which are similar to light coupler 1145 and image coupler 1145', respectively, disposed proximally of flange 1228. The absorbent member 1220 has a lumen therethrough in the nature of a slit 1269 having a cross or cruciform shape, as shown in FIG. 33, extending longitudinally through the absorbent member 1220.

When the absorbent member 1220 is in the dry state, the variable size passage 1269 defined by slit 1269 is closed due to the rigidity and stiffness of the absorbent member. The distal end 1224 of the absorbent member is used to penetrate an anatomical cavity wall, and the absorbent member 1220 absorbs body fluids to be placed in the wet state. In the wet state, the distal end 1224 becomes rounded or blunt as shown in dotted lines in FIG. 32, and the light and image transmitting optical element 1239" unbends or straightens as also shown in dotted lines in FIG. 32. The variable size passage 1269 can be expanded to receive an instrument introduced therethrough, with the absorbent member 1220 sealingly engaging the instrument in the variable size passage. The variable size passage 1269 returns to the initial position or size when the instrument is withdrawn. If desired, one or more spine members, such as spine member 1236 shown in dotted lines in FIG. 33, can be provided in the absorbent member 1220, and one or more light and/or image transmitting optical elements can form the spine member or members.

Another modification of an optical endoscopic portal is illustrated in FIG. 34 at 1310. Optical endoscopic portal 1310 is similar to optical endoscopic portal 1110 except that cannula 1312 for optical endoscopic portal 1310 is connected with a head 1314 and does not include an outer membrane. Cannula 1312 includes absorbent member 1320 having a blunt distal end 1324; however, the distal end 1324 can be tapered, sharp or pointed to facilitate penetration of a body cavity wall as shown in dotted lines in FIG. 34. A proximal end of absorbent member 1320 is coupled to head 1314 which has a truncated conical configuration with an opening 1356, shown in FIG. 35, in rearward wall 1354. The opening 1356 is aligned with a lumen or passage extending longitudinally through absorbent member 1320. As shown in FIG. 37, three tubular channel members 1367 extend longitudinally through the absorbent member 1320 and have distal ends aligned with the distal end 1324 and proximal ends connected with three ports 1344, respectively, protruding from head 1314. One port 1344 is utilized to supply fluid to the body cavity, another port 1344 is used for evacuation of fluid and substances from the body cavity and the third port 1344 can be used for supplying fluid to and/or evacuating fluid from the absorbent member 1320 in which case the channel member 1367 associated with the third port 1344 is provided with holes. A light transmitting optical element 1339 and an image transmitting optical element 1339' extend longitudinally through absorbent member 1320 and are coupled with light coupler 1345 and image coupler 1345', respectively, disposed on or adjacent head 1314 as shown in FIGS. 34, 35 and 36. The light and image transmitting optical elements 1339 and 1339', respectively, can be arranged in absorbent member 1320 in many various ways. In the case of optical endoscopic portal 1310, the light transmitting element 1339 and the image transmitting element 1339' are each disposed between two channel members 1367.

Liner 1316, shown in FIGS. 37 and 38, is disposed in the lumen of absorbent member 1320 and is similar to liner 1116 except that pleats 1372 of liner 1316 do not diminish in size at distal end 1324 since the distal end 1324 is not tapered. A distal end of the liner 1316 terminates at distal end 1324, and a proximal end of the liner 1316 terminates at or within head 1314. The opening 1356 in the rearward wall 1354 of the head 1314 is aligned with the variable size passage 1369 defined by liner 1316. The liner 1316 forms radial pleats 1372 uniformly spaced from one another and extending the same radial distance from the longitudinal axis of cannula 1312; however, the pleats 1372 can be non-radial and of random length and spacing.

Prior to use, the absorbent member 1320 is in the dry state. The lumen of the absorbent member 1320 through which the liner 1316 extends is large enough in the dry state to permit the variable size passage 1369 to be enlarged to receive an instrument, such as a Verres needle N shown in FIG. 38. Accordingly, even though the material of the absorbent member is disposed around the liner and between adjacent pleats 1372, the material does not completely fill the space around the inner bends of the pleats such that the variable size passage 1369 can still be opened a finite amount when the absorbent member 1320 is in the dry state. Where the distal end 1324 is blunt as shown in FIG. 34, a penetrating member or obturator, such as the Verres needle N, can be introduced through the variable size passage 1369 of liner 1316 for use in penetrating a body cavity wall. As shown in FIG. 38, introduction of needle N in variable size passage 1369 causes the variable size passage to enlarge to accommodate the needle N in sealing relation.

When the cannula 1312 is passed through a cavity wall W as shown in FIG. 36, the absorbent member 1320 absorbs body fluids and/or is supplied with fluid through one of the channel members 1367 to obtain the wet state. As shown in FIGS. 36 and 38, the absorbent member 1320 expands diametrically or radially in the wet state such that the cannula 1312 has an expanded configuration with an external diameter or cross-sectional size larger than the diameter or cross-sectional size of the cannula in the non-expanded configuration; however, the absorbent member 1320 does not have to expand in the wet state. Once the distal end 1324 of the cannula 1312 has entered the body cavity, the body cavity is illuminated via light transmitting optical element 1339 and a light source coupled therewith, and the body cavity is visualized via image transmitting optical element 1339' and a viewing device coupled therewith external of wall W. One or more spine members 1336, shown in dotted lines in FIG. 36, can be provided in the absorbent member 1320 to produce an external protuberance 1392 in the wet state, and the one or more spine members 1336 can include or be formed by one or more light and/or image transmitting optical elements such that the one or more light and/or image transmitting optical elements serve to rigidify and/or shape the cannula in the wet state. Upon withdrawal of Verres needle N from cannula 1312, the liner 1316 returns to a closed or initial position due to the bias of absorbent member 1320; and, where one or more spine members are provided in the absorbent member, the spine members assist in biasing the liner to the closed or initial position. Accordingly, the absorbent member 1320 maintains the variable size passage 1369 in the closed or initial position to prevent leakage through the optical endoscopic portal 1310 when no instrument passes therethrough while allowing the variable size passage 1369 to be enlarged from the closed or initial position to receive instruments of various sizes in sealing relation.

With the optical endoscopic portals of the present invention, cannulas are provided comprising elongate absorbent members having variable size passages therethrough for receiving instruments in sealing relation. The variable size passages can be of fixed size in the dry state for the absorbent members and of variable size in the wet state for the absorbent members. Alternatively, the variable size passages can be of variable size in both the dry and wet states. The absorbent members become soft and pliant in the wet state, with or without radial and/or longitudinal expansion; and, accordingly, the absorbent members do not have to be made of expandable materials. The absorbent members in the wet state maintain the variable size passages in an initial position, allow the variable size passages to be enlarged from the initial position to receive instruments and bias the variable size passages to return to the initial position upon withdrawal of the instruments. Where the variable size passages are not closed sufficiently in the initial position, or while an instrument is in place, to prevent fluid flow therethrough, conventional valves can be incorporated in the optical endoscopic portals. The distal ends of the absorbent members in the dry state can be configured to penetrate an anatomical cavity wall allowing the cannulas to be used as trocars or obturators; and, when the absorbent members are in the wet state, the distal ends become soft and blunt. The absorbent members can expand longitudinally in the wet state to perform a shielding function. The cannulas can be provided with safety shields maintained in a retracted position by the absorbent members in the dry state and released for movement to an extended position when the absorbent members are in the wet state, and the safety shields can be designed as modular components.

The cannulas can be provided with or without outer membranes; however, depending on the materials of the absorbent members, outer membranes can be beneficial in protecting the absorbent members and preventing any parts of the absorbent members from becoming detached in the patient's body. The cannulas can be provided with or without diametrically expandable passage defining members, which can include slit or split sleeves, elastic sleeves or spines, for example. The passage defining members can be maintained in a non-expanded position by the absorbent members in the dry state and allowed to move to an expanded position when the absorbent members are in the wet state.

The optical endoscopic portals can include various types of liners including pleated and non-pleated membranes, rolled members, slippery coatings including spray on coatings, folded, scrunched or squished members, meshes, overlapping or intermeshing leaves, rods, wires or filaments and universal seals. Where coatings are utilized as the liners, the coatings can be dry in the dry state and become slippery in the wet state. One exemplary coating material suitable for use as the liner along all or part of the lumen of the absorbent member is Aquavene made by Menlo Care of Menlo Park, Calif. In order to reduce friction associated with the introduction and withdrawal of instruments, the liners can extend less than the entire length of the optical endoscopic portals. The liners, which define the variable size passages, can be disposed in the cannulas and/or in housings or heads for the cannulas. Where disposed in the cannulas, the liners can extend the entire or less than the entire length of the cannulas. For example, the liners can be disposed at proximal ends of the cannulas, at distal ends of the cannulas or at intermediate locations along the cannulas. The liners can be segmented or discontinuous and can be disposed at more than one location. The absorbent members in the wet state bias the liners to the closed or initial position when no instruments are received in the variable size passages and into sealing engagement with instruments received in the variable size passages.

Universal seals and/or tubular expanders suitable for use in the optical endoscopic portals are disclosed in prior applications Ser. No. 08/618,328, filed Mar. 19, 1996 and Ser. No. 08/621,409, filed Mar. 25, 1996, the disclosures of which are incorporated herein by reference.

The absorbent members can be provided with various spine members for obtaining predetermined external configurations or shapes for the cannulas when the absorbent members are in the wet state and to add stiffness and rigidity to the absorbent members in the wet state. The spine members can be designed to provide one or more external protuberances or bubbles along the cannulas. The spine members can have various extended configurations to form various sizes and shapes of external protuberances including spherical, pear-shaped and triangular shaped protuberances, for example. The spine members can be utilized to supply fluids to the absorbent members, to supply fluids and other substances to the body cavities, to evacuate fluids from the absorbent members to facilitate withdrawal of the cannulas from the body cavities and to evacuate substances from the body cavities. Various medicaments or therapeutic agents can be introduced in the body cavities through the spine members.

The cannulas can be provided with channels or channel members extending therethrough for various purposes. Channels or channel members can be provided for supplying fluids to the absorbent members, evacuating fluids from the absorbent members, supplying fluids to the body cavities, supplying medicaments to the body cavities and evacuating substances from the body cavities. The fluids supplied to the absorbent members can include medicaments to be released in the body cavities and can also serve the function of placing the absorbent members in the wet state. Separate channels or channel members can be provided for the various purposes or functions, or the same channel or channel member can be used for more than one purpose or function.

The absorbent members can carry or be impregnated with various agents useful in the procedures to be performed. For example, the absorbent members can be impregnated or coated with medicaments or agents such as antibiotics, antiseptics, anesthetics, coagulants and anti-coagulants during or after manufacture such that the medicaments are carried, held or contained by or within the absorbent members in the dry state and are permitted to leak, leach or be released from the absorbent members in the wet state. In addition, medicaments and therapeutic agents can be supplied to the absorbent members and the patient's body via the channels, channel members and/or spines as discussed above. Accordingly, the cannulas can be utilized to deliver anesthetics directly to operative sites allowing more procedures to be performed endoscopically under local anesthesia. Various coatings can be applied to the absorbent members to control porosity or frictional characteristics in desired locations as well as to protect the materials of the absorbent members from damage due to stored springs and instruments, for example.

The speed of absorption of the absorbent members can be selected such that the cannulas remain stiff and, where applicable, sharp, until the cavity walls are penetrated. When the cannulas are in diametrically expanded configurations upon entry into the body cavities, the tissue of the cavity walls expands or stretches non-traumatically to accommodate the diametrically expanded cannulas and to accommodate further expansion of the cannulas via mechanical expansion thereof when instruments are introduced in the variable size passages. Accordingly, punctures or openings can be formed in the cavity walls corresponding in size to the initial cross sectional sizes of the cannulas, and the sizes of the punctures or openings can thereafter be enlarged non-traumatically due to expansion of the cannulas. The absorbent members can be used to apply pressure to control bleeding. The speed of absorption of the absorbent members can be selected such that the cannulas expand longitudinally once penetration through the cavity walls is accomplished whereby the cannulas serve as shields to protect the tips of the obturators. Various instruments or other objects can be introduced into and/or withdrawn from the body cavities through the optical endoscopic portals, and the instruments and objects can be introduced and withdrawn through tubular expanders introduced in the optical endoscopic portals to enlarge the variable size passages. Introduction and withdrawal of instruments and objects through tubular expanders has the advantage of reducing friction associated with introduction and withdrawal of instruments directly through the variable size passages.

The cannulas can be provided with selectively locatable constrictors or collars as disclosed in applicant's prior application Ser. No. 08/578,876, filed Dec. 22, 1995, the disclosure of which is incorporated herein by reference. The constrictors can be of different colors to serve as indicia identifying the locations of constrained portions of the cannulas. The cannulas can have externally visible bands or segments identifying the locations of protuberances. In addition, colored segments or bands can be provided to indicate depth of penetration.

The optical endoscopic portals according to the present invention have one or more light and/or image transmitting optical elements disposed in the materials of the absorbent members and/or in the compressible materials of the liners or seals. The one or more light and/or image transmitting optical elements can be designed as spine members and/or parts of spine members for the absorbent members and/or the liners such that the one or more light and/or image transmitting optical elements rigidify and/or shape the absorbent members and/or the compressible members of the liner. The light and/or image transmitting spine members can have various predetermined configurations in normal extended configurations and can be maintained in contracted configurations by the absorbent members in the dry state. When distal ends of the cannulas are positioned in body cavities through small size ports or passages, the one or more light and/or image transmitting optical elements illuminate the body cavities and/or transmit images of the body cavities for viewing externally thereof. Accordingly, illumination and visualization of a body cavity as well as introduction of instruments in the body cavity in sealing relation with a cannula can be accomplished with a single optical endoscopic portal.

In a smuch as the present invention is subject to many variations, modifications and changes in detail, it is intended that all subject matter discussed above or shown in the accompanying drawings be interpreted as illustrative only and not be taken in a limiting sense.

What is claimed is:

1. An optical endoscopic portal for providing a passage through a body cavity wall to provide access to a body cavity comprising an elongate absorbent member for being introduced through a small size opening in the body cavity wall and having a distal end for being positioned in the body cavity, a proximal end for being positioned externally of the body cavity wall and a lumen between said distal and proximal ends, said absorbent member being made of a material having a dry state prior to introduction through the body cavity wall and a wet state after absorbing fluid upon introduction of said distal end in the body cavity, said absorbent member being rigid in said dry state and being soft in said wet state, said lumen defining a variable size passage in said absorbent member in said wet state for receiving instruments of various cross sectional sizes in sealing relation; and an optical element carried by said absorbent member optically coupling said distal end with said proximal end.

2. An optical endoscopic portal as recited in claim 1 wherein said absorbent member has a first cross sectional size in said dry state and a second cross sectional size, greater than said first cross sectional size, in said wet state to sealingly engage the body cavity wall along the opening.

3. An optical endoscopic portal as recited in claim 2 wherein said absorbent member has a longitudinal axis and said absorbent member expands in a direction transverse to said axis in said wet state to form an external protuberance in said absorbent member.

4. An optical endoscopic portal as recited in claim 2 wherein said second cross sectional size is of a size to dilate the opening.

5. An optical endoscopic portal as recited in claim 1 wherein said absorbent member expands longitudinally in said wet state to increase the length of said absorbent member.

6. An optical endoscopic portal as recited in claim 1 wherein said optical element extends longitudinally through said absorbent member and is disposed within said material of said absorbent member.

7. An optical endoscopic portal as recited in claim 6 wherein said optical element is a light transmitting optical element for illuminating the body cavity.

8. An optical endoscopic portal as recited in claim 7 wherein said light transmitting optical element includes a plurality of light transmitting fibers disposed in an outer sheath.

9. An optical endoscopic portal as recited in claim 8 wherein said light transmitting optical element has a proximal end disposed external of the body cavity wall and said proximal end of said light transmitting optical element is coupled with a light source.

10. An optical endoscopic portal as recited in claim 6 wherein said optical element is an image transmitting optical element for transmitting an image of the body cavity for viewing externally of the body cavity wall.

11. An optical endoscopic portal as recited in claim 10 wherein said image transmitting optical element includes a plurality of image transmitting fibers disposed in an outer sheath.

12. An optical endoscopic portal as recited in claim 11 wherein said image transmitting optical element has a proximal end terminating external of the body cavity wall and said proximal end of said image transmitting optical element is coupled with a viewing device.

13. An optical endoscopic portal as recited in claim 6 wherein said optical element is a light and image transmitting optical element for illuminating the body cavity and for transmitting an image of the body cavity for viewing externally of the body cavity wall.

14. An optical endoscopic portal as recited in claim 13 wherein said light and image transmitting optical element includes a plurality of light transmitting fibers and a plurality of image transmitting fibers disposed in an outer sheath.

15. An optical endoscopic portal as recited in claim 14 wherein said light and image transmitting optical element has a proximal end terminating external of the body cavity wall and said light transmitting fibers are coupled with a light source and said image transmitting fibers are coupled with a viewing device at said proximal end of said light and image transmitting optical element.

16. An optical endoscopic portal as recited in claim 1 wherein said optical element forms a spine for shaping said absorbent member in said wet state.

17. An optical endoscopic portal as recited in claim 16 wherein said spine is disposed in a contracted configuration when said absorbent member is in said dry state and moves to an extended configuration when said absorbent member is in said wet state.

18. An optical endoscopic portal as recited in claim 17 wherein said spine includes at least one spine member having a trunk extending longitudinally through said absorbent member and having branches, said branches extending outwardly from said trunk in said extended configuration and said branches being disposed along side said trunk in said contracted configuration.

19. An optical endoscopic portal as recited in claim 18 wherein said optical element includes a plurality of optical fibers forming said trunk.

20. An optical endoscopic portal as recited in claim 17 wherein said optical element has a coiled configuration formed of a plurality of coils, said coils being disposed close to one another in said contracted configuration and being disposed further away from one another in said extended configuration.

21. An optical endoscopic portal as recited in claim 20 wherein at least some of said coils define a first diametric size in said contracted configuration and define a second diametric size, greater than said first diametric size, in said extended configuration to form an external protuberance in said absorbent member in said wet state.

22. An optical endoscopic portal as recited in claim 17 wherein said spine forms an external protuberance in said absorbent member when said spine is in said extended configuration with said absorbent member in said wet state.

23. An optical endoscopic portal as recited in claim 22 wherein said spine forms a plurality of external protuberances in said absorbent member when said spine is in said extended configuration with said absorbent member in said wet state.

24. An optical endoscopic portal as recited in claim 23 wherein said protuberances are longitudinally spaced from one another along said absorbent member.

25. An optical endoscopic portal as recited in claim 1 wherein said absorbent member is made of sponge material.

26. An optical endoscopic portal as recited in claim 1 wherein said absorbent member is made of a hydrogel forming composition.

27. An optical endoscopic portal for providing a passage through a body cavity wall to provide access to a body cavity comprising an elongate member for being introduced through a small size opening in the body cavity wall and having a distal end for being positioned in the body cavity, a proximal end for being positioned externally of the body cavity wall and a passage between said distal and proximal ends through which instruments are introduced in the body cavity, said elongate member being made of absorbent material and having a dry state prior to introduction through the body cavity wall and a wet state after absorbing fluid upon introduction of said distal end in the body cavity, said distal end of said elongate member being rigid and having a configuration in said dry state for penetrating the body cavity wall, said distal end of said elongate member being soft and blunt in said wet state to prevent damage to internal anatomical tissue; and an optical element carried by said absorbent material and optically coupling said distal end with said proximal end.

28. An optical endoscopic portal as recited in claim 27 wherein said optical element is a light transmitting optical element for illuminating the body cavity.

29. An optical endoscopic portal as recited in claim 28 and further including a light coupler coupled with said light transmitting optical element at said proximal end of said elongate member for coupling said light transmitting optical element with a light source.

30. An optical endoscopic portal as recited in claim 27 wherein said optical element is an image transmitting optical element for transmitting an image of the body cavity for viewing externally of the body cavity wall.

31. An optical endoscopic portal as recited in claim 30 and further including an image coupler coupled with said image transmitting optical element at said proximal end of said elongate member for coupling said image transmitting optical element with a viewing device.

32. An optical endoscopic portal as recited in claim 27 wherein said optical element is a light and image transmitting optical element for illuminating the body cavity and transmitting an image of the body cavity for viewing externally of the body cavity wall.

33. An optical endoscopic portal as recited in claim 32 and further including a light coupler and an image coupler coupled with said light and image transmitting optical element at said proximal end of said elongate member for coupling said light and image transmitting optical element with a light source and a viewing device.

34. An optical endoscopic portal as recited in claim 27 wherein said elongate member has a longitudinal axis and expands in a direction transverse to said axis in said wet state.

35. An optical endoscopic portal as recited in claim 27 wherein said passage is of fixed cross sectional size in said dry state and variable cross sectional size in said wet state to sealingly engage instruments of various cross sectional sizes introduced therethrough.

36. An optical endoscopic portal for providing a passage through a body cavity wall to provide access to a body cavity comprising a cannula for being introduced through a small size opening in the body cavity wall and having a distal end for being positioned in the body cavity, a proximal end for being positioned externally of the body cavity wall and a passage between said distal and proximal ends through which instruments are introduced in the body cavity, said cannula including an elongate member made of absorbent material and a membrane disposed over said elongate member, said elongate member having a dry state prior to introduction through the body cavity wall and a wet state after absorbing fluid upon introduction of said distal end in the body cavity; and an optical element disposed in said absorbent material optically coupling said distal end with said proximal end.

37. An optical endoscopic portal as recited in claim 36 wherein said membrane is made of stretchable material, said elongate member expands in said wet state and said membrane stretches to accommodate expansion of said elongate member.

38. An optical endoscopic portal as recited in claim 36 wherein said optical element forms an optical spine member for said elongate member, said optical spine member having a normal extended configuration, being maintained in a contracted configuration by said elongate member in said dry state and returning to said extended configuration when said elongate member is in said wet state to shape said elongate member to assume a predetermined external configuration in said wet state.

39. An optical endoscopic portal as recited in claim 36 wherein said membrane is transparent.

40. An optical endoscopic portal as recited in claim 36 and further including a liner in said elongate member defining said passage.

41. An optical endoscopic portal as recited in claim 36 and further including a channel through said cannula for supplying substances to the body cavity from external of the body cavity wall.

42. An optical endoscopic portal as recited in claim 36 and further including a channel through said cannula for evacuating substances from the body cavity from external of the body cavity wall.

43. An optical endoscopic portal as recited in claim 36 and further including a channel in said cannula for supplying fluid to said absorbent member.

44. An optical endoscopic portal as recited in claim 36 and further including a channel in said cannula for evacuating fluid from said absorbent member.

45. An optical endoscopic portal for providing a passage through a body cavity wall to provide access to a body cavity comprising
- a tubular sleeve for being introduced through a small size opening in the body cavity wall and having a distal end for being positioned in the body cavity, a proximal end for being positioned externally of the body cavity wall and a lumen between said distal and proximal ends for receiving instruments;
- a body of absorbent material disposed around said sleeve; and
- an optical element disposed in said absorbent material optically coupling said distal end with said proximal end.

46. An optical endoscopic portal as recited in claim 45 wherein said absorbent material has a rigid, dry state prior to absorbing fluid and a soft, wet state after absorbing fluid and said optical element forms a spine for shaping said absorbent material in said wet state, said optical element being disposed in a contracted configuration in said dry state and moving to an extended configuration when said absorbent material is in said wet state.

47. An optical endoscopic portal as recited in claim 46 wherein said sleeve is diametrically expandable to increase the cross sectional size of said lumen to receive instruments of various sizes.

48. A method of establishing a passage through a body cavity wall in endoscopic operative procedures comprising the steps of
- introducing an elongate member made of absorbent material in a small size opening in the body cavity wall with the elongate member in a rigid, dry state;
- positioning a distal end of the elongate member in the body cavity and a proximal end of the elongate member externally of the body cavity wall with the elongate member extending longitudinally through the opening in the body cavity wall;
- absorbing fluid with the absorbent material to place the elongate member in a soft, wet state;
- illuminating the body cavity with light transmitted by an optical element disposed in the absorbent material; and
- introducing an instrument through a longitudinal passage of the elongate member to position a distal end of the instrument in the body cavity.

49. A method of establishing a passage through a body cavity wall as recited in claim 48 wherein said step of introducing includes penetrating the body cavity wall with a penetrating member disposed in the longitudinal passage of the elongate member.

50. A method of establishing a passage through a body cavity wall as recited in claim 48 wherein said step of introducing includes penetrating the body cavity wall with the distal end of the elongate member.

51. A method of establishing a passage through a body cavity wall as recited in claim 48 wherein said step of absorbing includes contacting body fluid with the elongate member such that the absorbent material absorbs the body fluid.

52. A method of establishing a passage through a body cavity wall as recited in claim 48 wherein said step of absorbing includes supplying fluid to the absorbent material from externally of the body cavity.

53. A method of establishing a passage through a body cavity wall as recited in claim 48 wherein said step of absorbing includes moving the optical element from a contracted configuration to an extended configuration to shape the elongate member to assume a predetermined external configuration in response to absorption of fluid by the absorbent material.

54. A method of establishing a passage through a body cavity wall as recited in claim 48 wherein said step of absorbing includes expanding the elongate member diametrically in response to absorption of fluid by the absorbent material.

55. A method of establishing a passage through a body cavity wall as recited in claim 48 wherein said step of absorbing includes increasing the length of the elongate member longitudinally in response to absorption of fluid by the absorbent material.

56. A method of establishing a passage through a body cavity wall as recited in claim 48 and further including the step of transmitting an image of the body cavity via the optical element for viewing externally of the body cavity wall.

57. A method of establishing a passage through a body cavity wall comprising the steps of
- introducing an elongate member made of absorbent material in a small size opening in the body cavity wall with the elongate member in a rigid dry state;
- positioning a distal end of the elongate member in the body cavity and a proximal end of the elongate member externally of the body cavity wall with the elongate member extending longitudinally through the opening in the body cavity wall;
- absorbing fluid with the absorbent material to place the elongate member in a soft wet state;
- transmitting an image of the body cavity via an optical element disposed in the absorbent material; and
- introducing an instrument through a longitudinal passage of the elongate member to position a distal end of the instrument in the body cavity.

58. A method of establishing a passage through a body cavity wall as recited in claim 57 and further including the step of illuminating the body cavity with light transmitted by the optical element.

59. A method of establishing a passage through a body cavity wall as recited in claim 57 and further including the step of illuminating the body cavity with light transmitted by another optical element disposed in the absorbent material.

60. A method of establishing a passage through a body cavity wall as recited in claim 57 wherein said step of introducing includes penetrating the body cavity wall with a penetrating member disposed in the passage of the elongate member.

61. A method of establishing a passage through a body cavity wall as recited in claim 60 and further including the step of shielding the penetrating member with the elongate member in the wet state.

62. A method of establishing a passage through a body cavity wall as recited in claim 57 wherein said step of absorbing includes shaping the elongate member with the optical element when the elongate member is placed in the wet state.

63. A method of establishing a passage through a body cavity wall as recited in claim 57 wherein said step of introducing includes sealingly engaging the instrument with the elongate member.

\* \* \* \* \*